United States Patent
Bapat et al.

(10) Patent No.: US 12,253,527 B2
(45) Date of Patent: Mar. 18, 2025

(54) COMPOSITIONS AND METHODS FOR TREATING AGE-RELATED DIABETES AND RELATED DISORDERS

(71) Applicant: Salk Institute for Biological Studies, La Jolla, CA (US)

(72) Inventors: Sagar P. Bapat, La Jolla, CA (US); Ye Zheng, La Jolla, CA (US); Ronald Evans, La Jolla, CA (US); Michael Downes, La Jolla, CA (US); Annette R. Atkins, La Jolla, CA (US); Ruth T. Yu, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 287 days.

(21) Appl. No.: 17/813,383

(22) Filed: Jul. 19, 2022

(65) Prior Publication Data

US 2023/0078590 A1 Mar. 16, 2023

Related U.S. Application Data

(62) Division of application No. 16/702,870, filed on Dec. 4, 2019, now Pat. No. 11,428,697, which is a division of application No. 15/544,385, filed as application No. PCT/US2016/013004 on Jan. 12, 2016, now Pat. No. 10,539,572.

(60) Provisional application No. 62/154,652, filed on Apr. 29, 2015, provisional application No. 62/110,349, filed on Jan. 30, 2015.

(51) Int. Cl.
| | |
|---|---|
| *C07K 16/28* | (2006.01) |
| *A61K 39/395* | (2006.01) |
| *A61P 3/10* | (2006.01) |
| *C12Q 1/68* | (2018.01) |
| *C12Q 1/6883* | (2018.01) |
| *G01N 33/53* | (2006.01) |
| *G01N 33/68* | (2006.01) |
| *A61K 39/00* | (2006.01) |

(52) U.S. Cl.
CPC ....... *G01N 33/6869* (2013.01); *A61K 39/395* (2013.01); *A61P 3/10* (2018.01); *C07K 16/28* (2013.01); *C07K 16/2866* (2013.01); *C12Q 1/68* (2013.01); *C12Q 1/6883* (2013.01); *G01N 33/53* (2013.01); *A61K 2039/505* (2013.01); *C12Q 2600/118* (2013.01); *C12Q 2600/158* (2013.01); *G01N 2333/7155* (2013.01); *G01N 2800/042* (2013.01); *G01N 2800/50* (2013.01)

(58) Field of Classification Search
CPC ............... C07K 16/2866; C07K 16/28; G01N 2800/042; G01N 33/6869; A61P 3/10
See application file for complete search history.

(56) References Cited

U.S. PATENT DOCUMENTS

| | | | |
|---|---|---|---|
| 4,816,567 A | 3/1989 | Cabilly et al. | |
| 4,956,778 A | 9/1990 | Naito | |
| 5,091,513 A | 2/1992 | Huston et al. | |
| 5,132,405 A | 7/1992 | Huston et al. | |
| 5,225,539 A | 7/1993 | Winter | |
| 5,530,101 A | 6/1996 | Queen et al. | |
| 5,585,089 A | 12/1996 | Queen et al. | |
| 5,693,762 A | 12/1997 | Queen et al. | |
| 5,859,205 A | 1/1999 | Adair et al. | |
| 10,539,572 B2 | 1/2020 | Bapat et al. | |
| 2005/0196754 A1 | 9/2005 | Drmanac et al. | |
| 2012/0064100 A1 | 3/2012 | Barry et al. | |
| 2014/0004107 A1 | 1/2014 | Smith et al. | |
| 2018/0267059 A1 | 9/2018 | Bapat et al. | |
| 2020/0141947 A1 | 5/2020 | Bapat et al. | |

FOREIGN PATENT DOCUMENTS

WO 2016122865 A1 8/2016

OTHER PUBLICATIONS

Bapat et al., "Depletion of Fat Tregs Prevents Age-Associated Insulin Resistance," Nature, Dec. 3, 2015, vol. 528, No. 7580, pp. 137-141.
Cipolletta et al., "PPARγ is a major driver of the accumulation and phenotype of adipose-tissue Treg cells," Nature, Jun. 28, 2012, vol. 486, No. 7404, pp. 549-553.
Dobin et al., "STAR: ultrafast universal RNA-seq aligner," Bioinformatics, 2013, vol. 29, No. 1, pp. 15-21.
Feuerer et al., "Fat Treg cells: a liaison between the immune and metabolic systems," Nature Medicine, Aug. 2009, vol. 15, No. 8, pp. 930-939.
Gruber et al., "Efficient Tumor Cell Lysis Mediated by a Bispecific Single Chain Antibody Expressed in *Escherichia coli*," The Journal of Immunology, 1994, vol. 152, pp. 5368-5374.
He et al., "Adipose-specific peroxisome proliferator-activated receptor γ knockout causes insulin resistance in fat and iver but not in muscle," Proceedings of the National Academy of Sciences of the United States of America, Dec. 23, 2003, vol. 100, No. 26, pp. 15712-15717.

(Continued)

*Primary Examiner* — Gyan Chandra

(74) *Attorney, Agent, or Firm* — Greenberg Traurig, LLP; Melissa Hunter-Ensor; Leslie Serunian

(57) ABSTRACT

The invention features compositions and methods treating or preventing for age-related insulin resistance, type 2 diabetes and related disorders. The method involves depleting fTreg cells with an anti-ST2 antibody to decrease age-related fTreg accumulation and restore insulin sensitivity, thereby treating age-related insulin resistance, type 2 diabetes and related disorders.

16 Claims, 35 Drawing Sheets

Specification includes a Sequence Listing.

(56) References Cited

OTHER PUBLICATIONS

Holliger et al., "Diabodies': Small bivalent and bispecific antibody fragments," Proceedings of the National Academy of Sciences of the United States of America, Jul. 1993, vol. 90, No. 14, pp. 6444-6448.

Huston et al., "Protein engineering of antibody binding sites: Recovery of specific activity in an anti-digoxin single- chain Fv analogue produced in *Escherichia coli*," Proceedings of the National Academy of Sciences of the United States of America, Aug. 1988, vol. 85, pp. 5879-5883.

Kostelny et al., "Formation of a bispecific antibody by the use of leucine zippers," The Journal of Immunology, Mar. 1, 1992, vol. 148, No. 5, pp. 1547-1553.

Miller et al., "Interleukin-33 Induces Protective Effects in Adipose Tissue Inflammation During Obesity in Mice," Circulation Research, 2010, vol. 107, pp. 650-658.

Monticelli et al., "Innate lymphoid cells promote lung-tissue homeostasis after infection with influenza virus," Nature Immunology, Nov. 2011, vol. 12, No. 11, pp. 1045-1054.

Olafsen et al., "Covalent disulfide-linked anti-CEA diabody allows site-specific conjugation and radiolabeling for tumor targeting applications," Protein Engineering, Design and Selection, Jan. 2004, vol. 17, No. 1, pp. 21-27.

Palmer et al., "Inhibition of Interleukin-33 Signaling Attenuates the Severity of Experimental Arthritis," Arthritis & Rheumatism, Mar. 2009, vol. 60, No. 3, pp. 738-749.

Power et al., "Generation of Recombinant Multimeric Antibody Fragments for Tumor Diagnosis and Therapy," Recombinant Antibodies for Cancer Therapy, Methods in Molecular Biology Book Series, 2003, vol. 207, pp. 335-350.

Roberts et al., "Identification of novel transcripts in annotated genomes using RNA-Seq," Bioinformatics, 2011, vol. 27, No. 17, pp. 2325-2329.

Rubtsov et al., "Regulatory T Cell-Derived Interleukin-10 Limits Inflammation at Environmental Interfaces," Immunity, Apr. 2008, vol. 28, pp. 546-558.

Schiering et al., "The Alarmin IL-33 Promotes Regulatory T Cell Function in the Intestine," Nature, Sep. 25, 2014, vol. 513, No. 7519, pp. 564-568.

Trapnell et al., "Differential analysis of gene regulation at transcript resolution with RNA-seq," Nature Biotechnology, 2013, vol. 31, No. 1, pp. 46-53.

Tutt et al., "Activation and preferential expansion of rat cytotoxic (CD8) T cells in vitro and in vivo with a bispecific (anti-TCR alpha/beta x anti-CD2) F(ab')2 antibody," The Journal of Immunology, 1995, vol. 155, pp. 2960-2971.

Vasanthakumar et al., "The transcriptional regulators IRF4, BATF and IL-33 orchestrate development and maintenance of adipose tissue-resident regulatory T cells," Nature Immunology, 2015, pp. 1-12.

Wahl et al., "Improved Radioimaging and Tumor Localization with Monoclonal F(ab')2," The Journal of Nuclear Medicine, 1983, vol. 24, No. 4, pp. 316-325.

Wu et al., "High-resolution microPET imaging of carcinoembryonic antigen-positive xenografts by using a copper-64-labeled engineered antibody fragment," Proceedings of the National Academy of Sciences of the United States of America, Jul. 18, 2000, vol. 97, No. 15, pp. 8495-8500.

Zapata et al., "Engineering linear F(ab')2 fragments for efficient production in *Escherichia coli* and enhanced antiproliferative activity," Protein Engineering, 1995, vol. 8, No. 10, pp. 1057-1062.

Zeyda et al., "Severe obesity increases adipose tissue expression of interleukin-33 and its receptor ST2, both predominantly detectable in endothelial cells of human adipose tissue," International Journal of Obesity, 2013, vol. 37, pp. 658-665.

International Search Report and Written Opinion dated Apr. 22, 2016 in corresponding International PCT Patent Application No. PCT/US2016/013004 (13 pages).

fTregs are selectively enriched in aged mice.

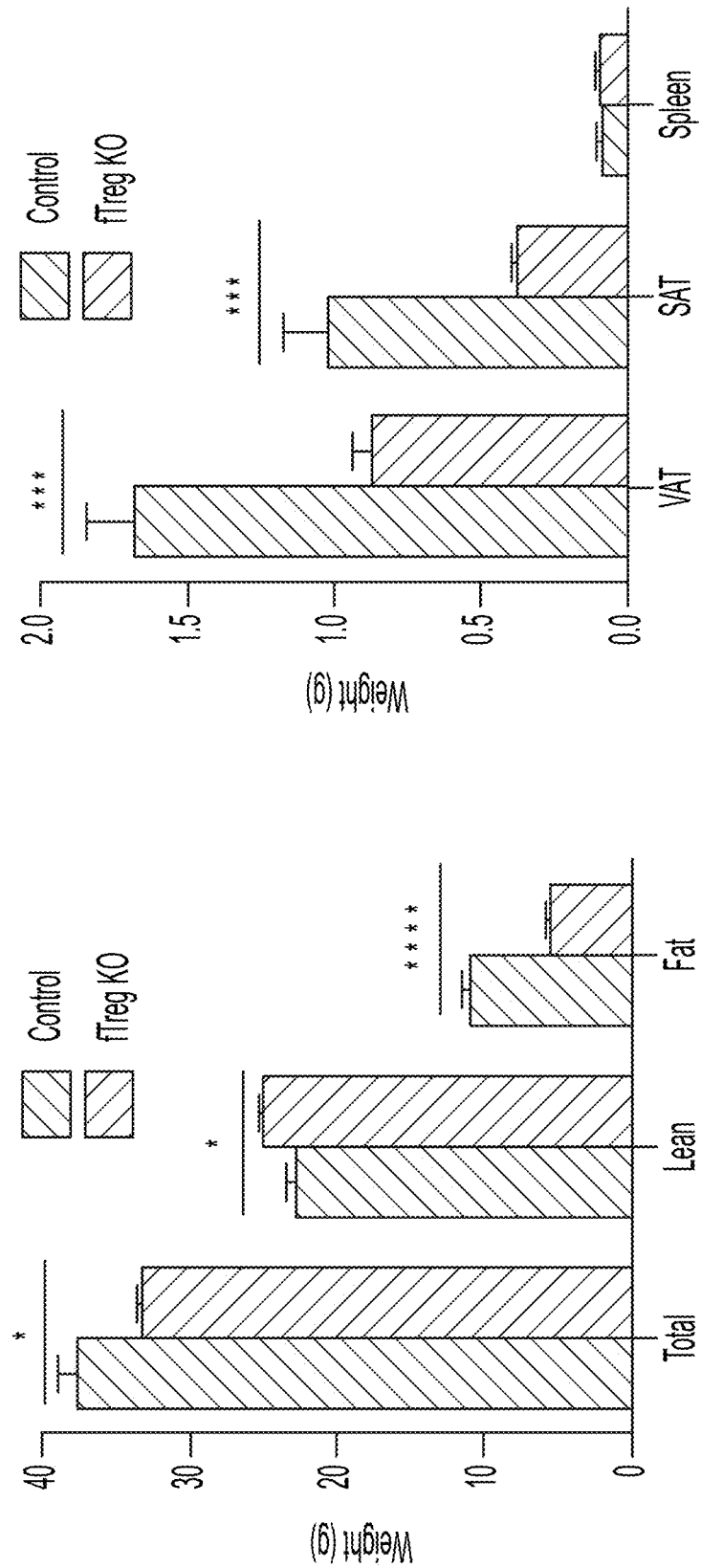

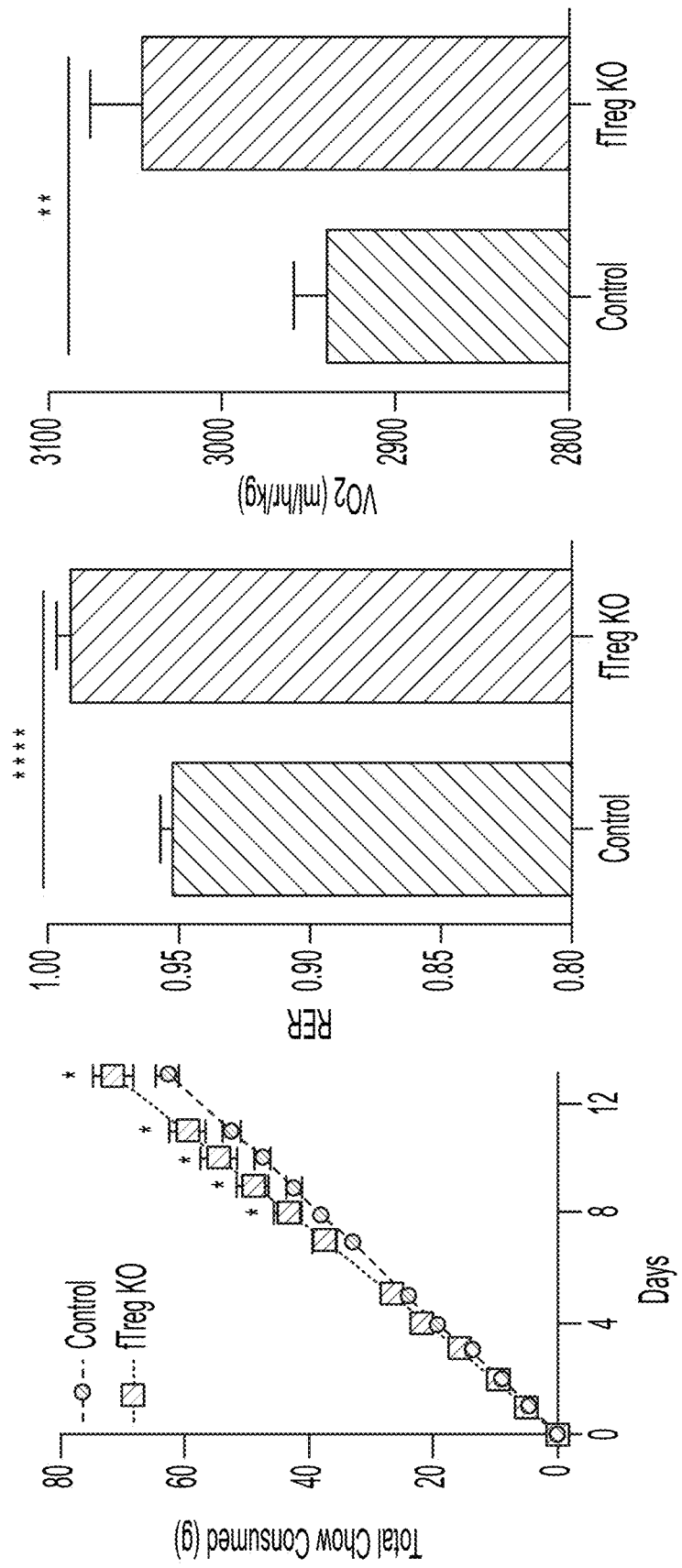

Loss of fTregs protects against the clinical hallmarks of age-associated metabolic dysregulation.

VAT Adipoimmune profiles of aged fTreg KO and control mice.

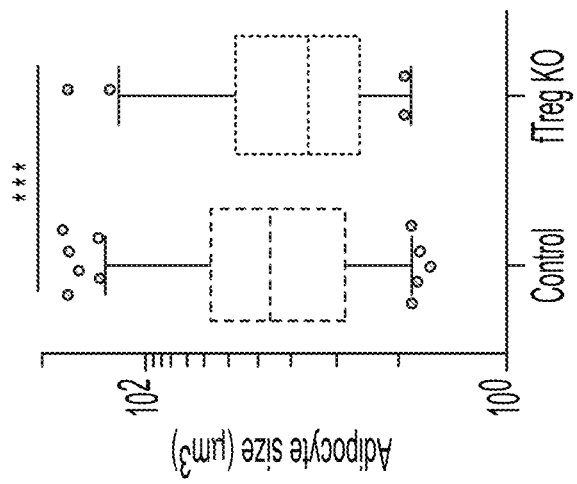
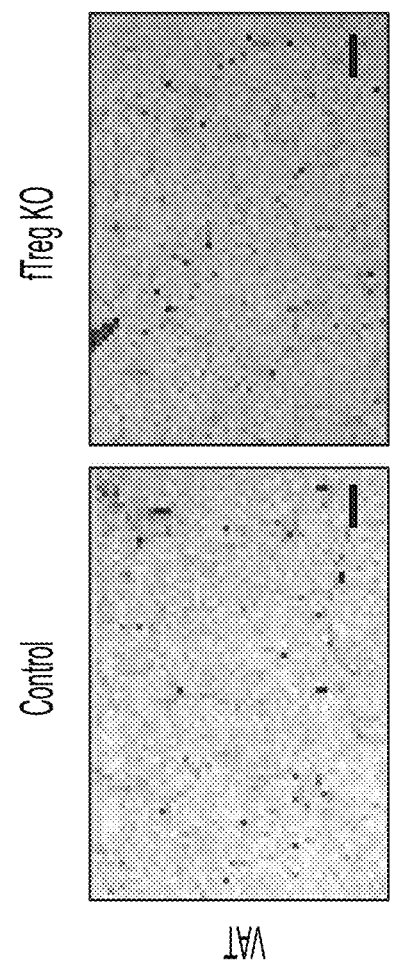
FIGURE 7G
FIGURE 7H fTreg gene expression.

fTreg depletion improves adipose glucose uptake fTreg depletion improves adipose glucose uptake

Depleting anti-ST2 antibody treatment does not promote T cell activation associated with systemic Treg-dysfunction.

SEQUENCE LISTING

```
Sequence total quantity: 1
SEQ ID NO: 1            moltype = AA   length = 556
FEATURE                 Location/Qualifiers
source                  1..556
                        mol_type = protein
                        organism = Homo sapiens
SEQUENCE: 1
MGFWILAILT ILMYSTAAKF SKQSWGLENE ALIVRCPRQG KPSYTVDWYY SQTNKSIPTQ   60
ERNRVFASGQ LLKFLPAAVA DSGIYTCIVR SPTFNRTGYA NVTIYKKQSD CNVPDYLMYS  120
TVSGSEKNSK IYCPTIDLYN WTAPLEWFKN CQALQGSRYR AHKSFLVIDN VMTEDAGDYT  180
CKFIHNENGA NYSVTATRSF TVKDEQGFSL FPVIGAPAQN EIKEVEIGKN ANLTCSACFG  240
KGTQFLAAVL WQLNGTKITD FGEPRIQQEE GQNQSFSNGL ACLDMVLRIA DVKEEDLLLQ  300
YDCLALNLHG LRRHTVRLSR KNPIDHHSIY CIIAVCSVFL MLINVLVIIL KMFWIEATLL  360
WRDIAKPYKT RNDGKLYDAY VVYPRNYKSS TDGASRVEHF VHQILPDVLE NKCGYTLCIY  420
GRDMLPGEDV VTAVETNIRK SRRHIFILTP QITHNKEFAY EQEVALHCAL IQNDAKVILI  480
EMEALSELDM LQAEALQDSL QHLMKVQGTI KWREDHIANK RSLNSKFWKH VRYQMPVPSK  540
IPRKASSLTP LAAQKQ                                                 556
```

COMPOSITIONS AND METHODS FOR TREATING AGE-RELATED DIABETES AND RELATED DISORDERS

CROSS-REFERENCE TO RELATED APPLICATIONS

This application is a divisional of patent application U.S. Ser. No. 16/702,870, filed on Dec. 4, 2019, which is a divisional of patent application U.S. Ser. No. 15/544,385, filed on Jul. 18, 2017, which is a U.S. National Stage Application pursuant to 35 U.S.C. § 371 of International PCT Application No.: PCT/US2016/013004, filed on Jan. 12, 2016, designating the United States and published in English, which claims priority to U.S. Provisional Patent Application Nos. 62/110,349, filed on Jan. 30, 2015, and 62/154,652, filed on Apr. 29, 2015. The contents of each of these applications are hereby incorporated by reference herein in their entireties.

STATEMENT OF RIGHTS TO INVENTIONS MADE UNDER FEDERALLY SPONSORED RESEARCH

This invention was made with government support under grant numbers DK096828, HL088093 and HL105278 awarded by the National Institutes of Health. The government has certain rights in the invention.

REFERENCE TO AN ELECTRONIC SEQUENCE LISTING

The present application contains a Sequence Listing which has been submitted electronically in XML format. The content of the electronic XML Sequence Listing, (Date of creation: Jul. 18, 2022; Size: 2,328 bytes; Name: 167776-010305USDIV2-Sequence_Listing.xml) is herein incorporated by reference in its entirety.

BACKGROUND OF THE INVENTION

Aging and obesity are the two primary etiologies of insulin resistance and diabetes, the defining epidemics of the modern world. While the complex interplay between the immune system and adipose tissue inflammation drives obesity-associated insulin resistance, the underlying mechanisms of aging-associated insulin resistance have yet to be determined. Age-associated insulin resistance is prevalent. In the US alone incidence of diabetes among adults, ages 65-79 years, has significantly increased from 6.9 per 1000 in 1980 to 15.4 per 1000 in 2011. Over 25% of all Americans over 60 years have type 2 diabetes and more than 50% are insulin resistant. Accordingly, methods of treating age-related insulin resistance, type 2 diabetes and related disorders are urgently needed.

SUMMARY OF THE INVENTION

As described herein below, the present invention features compositions and methods treating or preventing age-related insulin resistance, type 2 diabetes and related disorders. The method involves depleting fat-resident regulatory T cells (fTregs) cells with an anti-ST2 antibody to decrease age-related fTreg accumulation and restore insulin sensitivity, thereby treating age-related insulin resistance, type 2 diabetes and related disorders.

In one aspect, the invention provides a method of enhancing insulin sensitivity in a cell or tissue, the method involving contacting the cell or tissue with an anti-ST2 antibody or antigen binding fragment thereof, thereby decreasing the number of adipose-resident regulatory T cells (fTreg) and enhancing insulin sensitivity relative to a reference.

In another aspect, the invention provides a method of reducing insulin resistance in a cell or tissue, the method involving contacting the cell or tissue with an anti-ST2 antibody or antigen binding fragment thereof, thereby decreasing the number of adipose-resident regulatory T cells (fTreg) and reducing insulin resistance relative to a reference. In various embodiments, the cell is an adipocyte. In various embodiments, the tissue is adipose tissue.

In yet another aspect, the invention provides a method of enhancing insulin sensitivity in a subject, the method involving contacting the subject with an anti-ST2 antibody or antigen binding fragment thereof, thereby decreasing the number of adipose-resident regulatory T cells in the subject and enhancing insulin sensitivity relative to a reference.

In still another aspect, the invention provides a method of reducing insulin resistance in a subject, the method involving contacting the subject with an anti-ST2 antibody or antigen binding fragment thereof, thereby decreasing the number of adipose-resident regulatory T cells in the subject and reducing insulin resistance relative to a reference.

In another aspect, the invention provides a method for treating or preventing age-related insulin resistance, type 2 diabetes and related disorders in a subject, the method involving contacting the subject with an anti-ST2 antibody or antigen binding fragment thereof, thereby treating or preventing age-related insulin resistance, type 2 diabetes and related disorders in a subject.

In yet another aspect, the invention provides a method for treating or preventing age-associated metabolic dysregulation in a subject, the method involving contacting the subject with an anti-ST2 antibody or antigen binding fragment thereof, thereby treating or preventing age-associated metabolic dysregulation in the subject.

In one aspect, the invention provides a method for identifying a subject having or at risk of developing age-related insulin resistance, type 2 diabetes and related disorders, the method involving detecting an increase in an ST2 polypeptide or polynucleotide expression in an fTreg or detecting an increase in the number of fTregs relative to a control. In one embodiment the fTreg is present in a tissue biopsy. In another embodiment the tissue biopsy if obtained from visceral adipose tissue. In still another embodiment the ST2 polypeptide is detected in an immunoassay.

In another aspect, the invention provides a method of reducing insulin resistance in a subject, the method involving administering to the subject an anti-ST2 antibody or antigen binding fragment thereof, wherein the subject is identified as having an increase in an ST2 polypeptide or polynucleotide expression in an fTreg or detecting an increase in the number of fTregs relative to a control. In one embodiment the subject has or is at risk of developing age-related insulin resistance.

In one aspect, the invention provides a kit for treating or preventing age-related insulin resistance, the kit containing an effective amount of an ST2 antibody in a pharmaceutical excipient.

In various embodiments of any of the previous aspects or any other aspect of the invention delineated herein, the subject is fifty, sixty, or sixty-five, years old or older. In various embodiments of any of the previous aspects or any other aspect of the invention delineated herein, the method reduces body weight relative to a reference. In various embodiments of any of the previous aspects or any other aspect of the invention delineated herein, the method decreased visceral adipose tissue and/or subcutaneous adipose tissue adiposity relative to a reference. In various embodiments of any of the previous aspects or any other aspect of the invention delineated herein, the method increases respiratory exchange ratio, oxygen consumption, and/or core body temperature relative to a reference.

In various embodiments of any of the previous aspects or any other aspect of the invention delineated herein, the method reduces fasting serum glucose and insulin levels relative to a reference. In various embodiments said method reduces glucose excursions during a glucose tolerance test and/or increases sensitivity during an insulin tolerance test relative to a reference. In various embodiments said method reduces serum non-esterified free fatty acid (NEFA) levels relative to a reference. In various embodiments said method increases insulin sensitivity relative to a reference. In various embodiments said method decreases hepatic steatosis relative to a reference. In various embodiments said method decreases fasting hepatic and/or serum triglyceride content.

In various embodiments of any of the previous aspects or any other aspect of the invention delineated herein, the method does not produce an autoimmune syndrome. In various embodiments said method specifically decreases fTreg numbers while preserving splenic Treg numbers. In various embodiments said method increases the glucose uptake capacity of visceral adipose tissue compared to a reference. In various embodiments of any of the previous aspects or any other aspect of the invention delineated herein, the anti-ST2 antibody administration is parenterally.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "ST2 (Interleukin 1 receptor-like 1) protein" is meant a protein having at least about 85%, 90%, 95%, or 100% amino acid identity to NCBI Accession No. Q01638 or a fragment thereof that binds IL-33.

An exemplary amino acid sequence is provided below.

```
>sp|Q01638|ILRL1_HUMAN Interleukin-1
receptor-like 1 OS = Homo sapiens
GN = IL1RL1 PE = 1 SV = 4
                               (SEQ ID NO: 1)
MGFWILAILTILMYSTAAKFSKQSWGLENE

ALIVRCPRQGKPSYTVDWYYSQTNKSIPTQ

ERNRVFASGQLLKFLPAAVADSGIYTCIVR

SPTFNRTGYANVTIYKKQSDCNVPDYLMYS

TVSGSEKNSKIYCPTIDLYNWTAPLEWFKN
```

-continued
```
CQALQGSRYRAHKSFLVIDNVMTEDAGDYT

CKFIHNENGANYSVTATRSFTVKDEQGFSL

FPVIGAPAQNEIKEVEIGKNANLTCSACFG

KGTQFLAAVLWQLNGTKITDFGEPRIQQEE

GQNQSFSNGLACLDMVLRIADVKEEDLLLQ

YDCLALNLHGLRRHTVRLSRKNPIDHHSIY

CIIAVCSVFLMLINVLVIILKMFWIEATLL

WRDIAKPYKTRNDGKLYDAYVVYPRNYKSS

TDGASRVEHFVHQILPDVLENKCGYTLCIY

GRDMLPGEDVVTAVETNIRKSRRHIFILTP

QITHNKEFAYEQEVALHCALIQNDAKVILI

EMEALSELDMLQAEALQDSLQHLMKVQGTI

KWREDHIANKRSLNSKFWKHVRYQMPVPSK

IPRKASSLTPLAAQKQ
```

By "ST2 (Interleukin 1 receptor-like 1) antibody" is meant an antibody or antigen binding fragment thereof that specifically binds an ST2 polypeptide or fragment thereof. Such antibodies are known in the art and commercially available. A mouse anti-human ST2 antibody is available, for example, from Novus Biologicals. Other anti-human ST2 antibodies are known in the art (e.g., Palmer et al., *Arthritis Rheum.* 2009 March; 60(3):738-49).

By "fat-resident regulatory T cell (fTreg)" is meant a regulatory T cell that is resident in adipose tissue. In one embodiment, an fTreg expresses Foxp3. In another embodiment, an fTreg expresses an increased level of ST2 relative to a splenic Treg of fat conventional CD4$^+$ T cells. For example, ST2 is at least about 10, 20, 30, 40, 50, or 60 times more highly expressed in an fTreg compared to a splenic Treg.

By "ameliorate" is meant decrease, suppress, attenuate, diminish, arrest, or stabilize the development or progression of a disease.

By "agent" is meant any small molecule chemical compound, antibody, nucleic acid molecule, or polypeptide, or fragments thereof.

By "alteration" is meant a change (increase or decrease) in the levels or activity of an analyte detected by standard art known methods such as those described herein. As used herein, an alteration includes a 10% change in analyte levels, preferably a 25% change, more preferably a 40% change, and most preferably a 50% or greater change in analyte levels. In one embodiment, an analyte is a cell, such as a fat regulatory T cells (fTreg).

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

By "biopsy" is meant a test involving sampling of cells or tissues for examination by removing tissue from a living subject to determine the presence or extent of a disease. Examples of biopsies include removal of visceral adipose tissues or cells.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. Examples of diseases include age-related insulin resistance, type 2 diabetes and related disorders. Related disorders include metabolic disorders characterized by an increase in the number of fTregs.

By "effective amount" is meant the amount of an agent of the invention (e.g., antibody or antigen binding fragment thereof) required to ameliorate the symptoms of a disease relative to an untreated patient. In one embodiment, an effective amount is the amount required to significantly reduce the number of fat-resident regulatory T cells in a adipose tissue relative to the number present in an untreated control. The effective amount of active agent used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein, "obtaining" as in "obtaining an agent" includes synthesizing, purchasing, or otherwise acquiring the agent.

By "reduces" is meant a negative alteration of at least 10%, 25%, 50%, 75%, or 100%.

By "reference" is meant a standard or control condition.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A is a schematic showing the etiologies for obesity-versus age-related insulin resistance in mice. FIG. 1B depicts pie charts showing visceral adipose tissue (VAT) adipo-immune profiles (AIP) from mice at 12 weeks (young, n=10), 44 weeks (aged, n=10), and in diet-induced obese (DIO) mice (n=10). Immune cells abundance, expressed as percentage of CD45.2$^+$ cells. FIG. 1C is a bar graph comparing changes in immune cell abundance between indicated groups, expressed as fold change in cell number per gram of VAT. #, false discovery rate<2%. Obese mice were fed a high fat diet for 12 weeks from 12 weeks of age. Data represents mean±standard error of the mean (s.e.m).

FIGS. 2A-2C, using Foxp3$^{cre\text{-}YFP}$ reporter mice, show how the stromal vascular fraction of visceral adipose tissue (VAT) was analyzed by flow cytometry to identify several T cell subtypes (FIG. 2A), macrophage subsets (FIG. 2B), and eosinophils and neutrophils (FIG. 2C).

FIGS. 3A-3H are scatter plots, linear, and bar graphs showing that fTreg knock out (KO) mice were protected from general hallmarks of metabolic aging. FIG. 3A is a scatter plot showing representative Fluorescence Activated Cell Sorting (FACS) plots of fTreg KO (Foxp3$^{Cre}$ PPARg$^{fl/fl}$) and control (Foxp3$^{Cre}$ PPARg$^{+/+}$) mice depicting Treg enrichment in visceral adipose tissue (VAT) and spleen. FIG. 3B is a bar graph showing total body weight (n=15 per group), and lean and fat mass of control and fTreg KO mice (~12 months, n=8 per group). FIG. 3C is a bar graph showing mass of VAT, subcutaneous adipose tissue (SAT), and spleen in aged control and fTreg KO mice (~15 months, n=9 per group). FIG. 3D is a linear graph showing cumulative food consumption of control and fTreg KO mice (~8-9 months old, n=8 per group). FIG. 3E and FIG. 3F are bar graphs showing average 24 hour respiratory exchange ratio (RER) of (FIG. 3E) and average VO$_2$ (FIG. 3F) consumed by aged control and fTreg KO mice (~11 months, n=6 per group). FIG. 3G is a bar graph showing core body temperature of control and fTreg mice (~13 months old, n=9 per group). FIG. 3H is a scatter plot showing principal component analysis of non-macrophage adipoImmune Profiles (AIPs) of young (12 weeks), aged (~15 months) and aged-fTreg KO (~15 months) mice. Data represents mean±s.e.m. *p<0.05, p<0.01, *p<0.001, ****p<0.0001.

FIG. 4A presents pie charts showing adipoImmune Profiles of aged (~14 months old) fTreg KO and control mice male mice depicting immune cell abundance, expressed as percentage of CD45.2$^+$ cells. Entirety of immune compartment (top) was further divided into pan-macrophage (middle) and non-macrophage (bottom) pie charts (n=9 mice per group). FIG. 4B is a bar graph showing immune cell abundance between fTreg KO and control mice, expressed as cells per gram of VAT (n=9 mice per group). #, false discovery rate<2%. Data represents mean±s.e.m.

FIGS. 5A and 5B compare immune cell abundance between fTreg KO and control mice, expressed as cells per gram of subcutaneous adipose tissue (SAT, FIG. 5A) and spleen (FIG. 5B) (n=9 mice per group). Data represents mean±s.e.m.

FIG. 6A is a bar graph showing percentage of splenic naive CD4$^+$ T cells as defined by CD62$^{hi}$ CD44$^{lo}$ relative to total CD4$^+$ Foxp3-YFP$^-$ CD25$^-$ population (n=9 mice per group). FIG. 6B are eight representative histology images of gastrointestinal tract—duodenum, jejunum, ileum, and colon (left to right), (n=3 mice per group). There were no significant lesions observed or differences in inflammation, epithelial changes, or mucosal architecture between the two groups (hematoxylin and eosin (H&E), ×100, scale bar 50 µm). FIG. 6C is a bar graph comparing the histopathology score in the small intestine and colon of fTreg KO and control mice. The severity and extent of inflammation and epithelial changes as well as mucosal architecture were each graded on a score of 1 (minimal) to 5 (severe) and added to obtain an overall score over 20. There were minimal inflammatory changes with no significant differences between groups. FIG. 6D is a bar graph showing a multiplex inflammation panel of serum from fTreg KO and control mice (n=4 pooled samples (3 mice per sample) per group).

FIG. 7A is a bar graph showing fTreg levels in visceral adipose tissue (VAT) from control and fTreg KO (Foxp3$^{Cre}$ PPARg$^{fl/fl}$) mice in young (control n=6; fTreg KO n=6), aged (~15 months old; control n=10; fTreg KO n=10), and obese mice (control n=6; fTreg KO n=8). FIG. 7G shows four representative images of hematoxylin and eosin (H&E) staining of visceral adipose tissue (VAT, gonadal) from ~14 month old control (n=3) and fTreg KO mice (n=5) (scale bar, 50 µM). FIG. 7H is a box and whisker plot of adipocyte size distribution in visceral adipose tissue from control (n=3) and fTreg KO mice (n=3) (~14 months old).

7L is a bar graph showing representative images of hematoxylin and eosin (H&E) staining of liver from ~14 month old control (n=3) and fTreg KO mice (n=5) (scale bar, 200 μM). FIG. 7P is a bar graph showing relative glucose uptake in VAT of 16 week old wild-type and IL2/anti-IL2 treated mice (n=4 mice per group). Data represents mean±s.e.m. *$p<0.05$, $p<0.01$, *$p<0.001$, ****$p<0.0001$.

FIG. 9A presents pie charts of adipoImmune profiles of obese (diet-induced obese (DIO), 16 weeks high fat diet (HFD) started at 12 weeks of age) control (n=6 mice) and fTreg KO (n=8 mice) male mice depicting immune cell abundance, expressed as percentage of $CD45.2^+$ cells. Entirety of immune compartment (top) was further divided into pan-macrophage (middle) and non-macrophage (bottom) pie charts. FIG. 9B is a bar graph showing immune cell abundance between fTreg KO and control mice, expressed as cells per gram of VAT (n=9 mice per group). Data represents mean±s.e.m.

FIG. 11A is a heat map showing expression of several canonical Treg genes across fat and splenic Tregs and fat and splenic Tconv cells. Cells were pooled from 3 and 4 mice before isolating RNA for subsequent RNA-Seq analysis. FIG. 11B is a scatter plot comparing expression of ST2 across all hematopoietic cells catalogued in the Immunological Genome Project database. Position of adipose $CD4^+CD25^+$ T cells is marked.

FIG. 12A and FIG. 12B are a heat map and a scatter plot showing hierarchical clustering of differentially expressed genes between fat Tregs and Tconv and splenic Tregs and Tconv cells (FIG. 12A), and fold change in expression levels of differentially expressed genes (FIG. 12B) across fat Tregs and Tconv and splenic Tregs and Tconv cells from Foxp3-Thy1.1 mice (47 weeks, cells pooled from 3 to 4 mice). Fat Treg cluster genes are labeled in red. Position of ST2 is marked. FIG. 12C and FIG. 12D are a line graph and a bar graph showing representative FACS analysis (FIG. 12C) and quantification of ST2 expression (FIG. 12D) in $CD4^+$ T cells from aged mice (45 weeks, n=5 mice). FIG. 12E is a bar graph comparing total number of $ST2^+$ Tregs and Tconv cells per gram of tissue in visceral adipose tissue (VAT) and spleen (n=5 mice). FIG. 12F is a line graph of FACS histograms, FIG. 12G is a bar graph showing quantification of Tregs (% Foxp3$^+$ of $CD45^+CD4^+$ population), and FIG. 12H is a bar graph depicting cells per gram of tissue in VAT and spleen after IL-33 or PBS treatment (16 weeks, n=5 mice per group). FIG. 12I is a bar graph showing ex vivo glucose uptake in VAT from wild type mice after control or IL-33 treatment (16 weeks, n=5 mice per group). FIG. 12J is a bar graph showing percentages of $CD4^+$, fTreg, and $CD4^+$ Tconv cells in VAT, and FIG. 12K is a bar graph showing ex vivo insulin stimulated glucose uptake in VAT from wild type mice after anti-ST2 depleting antibody or isotype control treatment (~45 weeks old, n=4 mice per group). FIG. 12L is schematic of an adipo-immune model of metabolic aging. Data represents mean±s.e.m. *$p<0.05$, **$p<0.01$.

FIG. 13A is a bar graph comparing total weight before beginning course of anti-ST2 or isotype control antibodies (Day 0) and upon terminal analysis. FIG. 13B and FIG. 13C are two bar graphs showing spleen weight (FIG. 13B) and percentage of splenic naive $CD4^+$ T cells as defined by $CD62^{hi}$ $CD44^{lo}$ relative to total splenic $CD45^+CD4^+$ $CD25^-$ T cell population (FIG. 13C) of mice upon terminal analysis (Day 3, n=4 mice per group).

DETAILED DESCRIPTION OF THE INVENTION

Figure 1A:
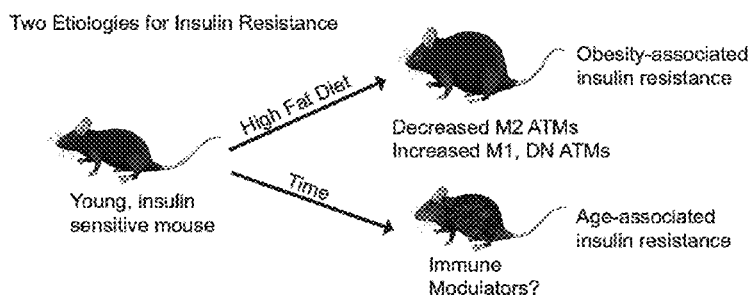
FIGS. 1A-1C are a schematic and pie charts showing that fTregs were selectively enriched in aged mice.

As described herein below, the present invention features compositions and methods for treating or preventing age-related insulin resistance, type 2 diabetes and related disorders. The method involves depleting fTreg cells with an anti-ST2 antibody to decrease age-related fTreg accumulation and restore insulin sensitivity, thereby treating age-related insulin resistance, type 2 diabetes and related disorders.

The invention is based, at least in part, on the discovery that adipose (fat)-resident regulatory T cells (fTregs) accumulate in adipose tissue as a function of age, and their accumulation in adipose is a driver of age-associated insulin resistance. Treatment with anti-ST2 antibodies depleted fTregs while preserving splenic Treg numbers. Additionally adipose from aged mice treated with anti-ST2 antibody had increased insulin sensitivity compared to controls.

Age-associated insulin resistance and obesity-associated insulin resistance are two physiologically distinct forms of adult onset diabetes. While macrophage-driven inflammation is a core driver of obesity-associated insulin resistance, the underlying mechanisms of the obesity-independent yet highly prevalent age-associated insulin resistance are largely unexplored. Comparative adipo-immune profiling revealed that fat-resident regulatory T cells, termed fTregs, progressively accumulated in adipose tissue as a function of age, but not obesity. Supporting the existence of two distinct mechanisms underlying age-associated versus obesity-associated insulin resistance, mice deficient in fTregs were protected against age-associated insulin resistance, yet remained susceptible to obesity-associated insulin resistance and metabolic disease. In contrast, selective depletion of fTregs via anti-ST2 antibody treatment increased adipose tissue insulin sensitivity. These findings established that distinct immune cell populations within adipose tissue underlie aging- and obesity-associated insulin resistance and implicated fTregs as adipo-immune drivers and potential therapeutic targets in the treatment of age-associated insulin resistance.

The immune system is complex, and the relative populations of different immune cells within adipose tissue are essentially uncharacterized. To better understand the immune system in aged adipose tissue, a quantitative, global picture of the immune system within adipose tissue was assembled using AdipoImmune Profile and fluorescence activated cell sorting (FACS).

Fat-resident regulatory T cells, termed fTregs, drove age-associated insulin resistance and can be specifically depleted to increase adipose insulin sensitivity. Comparative AdipoImmune profiling in young, aged, and obese mice revealed that fTregs progressively enriched in adipose as a function of age, but not obesity. fTreg-deficient mice were protected from age-associated insulin resistance and its accompanying physiological hallmarks. In contrast, fTreg-deficiency offered no protection from obesity-associated insulin resistance. One general problem about studying tissue-specific immune cells is that there is generally not a clean way of depleting, expanding, or perturbing a given immune cell type in a tissue-specific manner. Leveraging the high differential expression of ST2 in fTregs compared to splenic Tregs, it was found that treatment with anti-ST2 antibody depletes fTregs and increases adipose insulin sensitivity while preserving splenic Treg numbers. Taken together, it was demonstrated that distinct immunophysiologies underlie aging-versus obesity-associated insulin resistance and posit fTregs as adipoimmune drivers of and potential therapeutic targets against age-associated insulin resistance. Accordingly, the invention provides methods featuring an anti-ST2 antibody for enhancing insulin sensitivity in adipose tissue, and treating age-related insulin resistance, type 2 diabetes and related disorders.

ST2 Antibodies

Antibodies that selectively bind ST2 are useful in the methods of the invention. Methods of preparing antibodies are well known to those of ordinary skill in the science of immunology. As used herein, the term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and may have less non-specific tissue binding of an intact antibody (Wahl et al., *J. Nucl. Med.* 24:316-325 (1983). The antibodies of the invention comprise whole native antibodies, bispecific antibodies; chimeric antibodies; Fab, Fab', single chain V region fragments (scFv), fusion polypeptides, and unconventional antibodies.

Unconventional antibodies include, but are not limited to, nanobodies, linear antibodies (Zapata et al., Protein Eng. 8(10): 1057-1062, 1995), single domain antibodies, single chain antibodies, and antibodies having multiple valencies (e.g., diabodies, tribodies, tetrabodies, and pentabodies). Nanobodies are the smallest fragments of naturally occurring heavy-chain antibodies that have evolved to be fully functional in the absence of a light chain. Nanobodies have the affinity and specificity of conventional antibodies although they are only half of the size of a single chain Fv fragment. The consequence of this unique structure, combined with their extreme stability and a high degree of homology with human antibody frameworks, is that nanobodies can bind therapeutic targets not accessible to conventional antibodies. Recombinant antibody fragments with multiple valencies provide high binding avidity and unique targeting specificity to cancer cells. These multimeric scFvs (e.g., diabodies, tetrabodies) offer an improvement over the parent antibody since small molecules of ~60-100 kDa in size provide faster blood clearance and rapid tissue uptake See Power et al., (Generation of recombinant multimeric antibody fragments for tumor diagnosis and therapy. Methods Mol Biol, 207, 335-50, 2003); and Wu et al. (Anti-carcinoembryonic antigen (CEA) diabody for rapid tumor targeting and imaging. Tumor Targeting, 4, 47-58, 1999).

Various techniques for making and unconventional antibodies have been described. Bispecific antibodies produced using leucine zippers are described by Kostelny et al. (J. Immunol. 148(5):1547-1553, 1992). Diabody technology is described by Hollinger et al. (Proc. Natl. Acad. Sci. USA 90:6444-6448, 1993). Another strategy for making bispecific antibody fragments by the use of single-chain Fv (sFv) diners is described by Gruber et al. (J. Immunol. 152:5368, 1994). Trispecific antibodies are described by Tutt et al. (J. Immunol. 147:60, 1991). Single chain Fv polypeptide antibodies include a covalently linked VH::VL heterodimer which can be expressed from a nucleic acid including $V_H$- and $V_L$-encoding sequences either joined directly or joined by a peptide-encoding linker as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754.

In one embodiment, an antibody that binds ST2 is monoclonal. Alternatively, the anti-ST2 antibody is a polyclonal antibody. The preparation and use of polyclonal antibodies are also known the skilled artisan. The invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(ab)₂" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fab fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Antibodies can be made by any of the methods known in the art utilizing ST2 polypeptide, or immunogenic fragments thereof, as an immunogen. One method of obtaining antibodies is to immunize suitable host animals with an immunogen and to follow standard procedures for polyclonal or monoclonal antibody production. The immunogen will facilitate presentation of the immunogen on the cell surface. Immunization of a suitable host can be carried out in a number of ways. Nucleic acid sequences encoding an ST2 polypeptide or immunogenic fragments thereof, can be provided to the host in a delivery vehicle that is taken up by immune cells of the host. The cells will in turn express the receptor on the cell surface generating an immunogenic response in the host. Alternatively, nucleic acid sequences encoding a ST2 polypeptide, or immunogenic fragments thereof, can be expressed in cells in vitro, followed by isolation of the receptor and administration of the receptor to a suitable host in which antibodies are raised.

Alternatively, antibodies against an ST2 polypeptide may, if desired, be derived from an antibody phage display library. A bacteriophage is capable of infecting and reproducing within bacteria, which can be engineered, when combined with human antibody genes, to display human antibody proteins. Phage display is the process by which the phage is made to 'display' the human antibody proteins on its surface. Genes from the human antibody gene libraries are inserted into a population of phage. Each phage carries the genes for a different antibody and thus displays a different antibody on its surface.

Antibodies made by any method known in the art can then be purified from the host. Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

Antibodies can be conveniently produced from hybridoma cells engineered to express the antibody. Methods of making hybridomas are well known in the art. The hybridoma cells can be cultured in a suitable medium, and spent medium can be used as an antibody source. Polynucleotides encoding the antibody of interest can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition (e.g., Pristane).

Monoclonal antibodies (Mabs) produced by methods of the invention can be "humanized" by methods known in the art. "Humanized" antibodies are antibodies in which at least part of the sequence has been altered from its initial form to render it more like human immunoglobulins. Techniques to humanize antibodies are particularly useful when non-human animal (e.g., murine) antibodies are generated. Examples of methods for humanizing a murine antibody are provided in U.S. Pat. Nos. 4,816,567, 5,530,101, 5,225,539, 5,585,089, 5,693,762 and 5,859,205.

Diagnostics

The present invention features diagnostic assays for the detection of age-related insulin resistance, type 2 diabetes and related disorders or the propensity to develop such conditions. In one embodiment, levels of ST2 polypeptides and/or polynucleotides are measured in a subject sample (e.g., adipose tissue, fTregs) and used as an indicator of age-related insulin resistance, type 2 diabetes and related disorders or the propensity to develop such conditions. In another embodiment, the number of fTregs are measured in a subject sample (e.g., adipose tissue) and used as an indicator of age-related insulin resistance, type 2 diabetes and related disorders or the propensity to develop such conditions. Detection of an increase in an ST2 polypeptide or polynucleotide expression in an fTreg or detecting an increase in the number of fTregs in the sample relative to a control is indicative of age-related insulin resistance, type 2 diabetes and related disorders or the propensity to develop such conditions.

Standard methods may be used to measure levels of ST2 polypeptides and/or polynucleotides in fTregs. Such methods include immunoassay, ELISA, western blotting using an anti-ST2 antibody, and radioimmunoassay. Methods for measuring the number of fTregs present in a sample are known in the art and described herein below (e.g., using adipose immune profiling).

Diagnostic Kits

The invention also provides for a diagnostic test kit that comprises an antibody or other means for detecting an ST2 polypeptide. Desirably, the kits includes instructions for the use of the kit in the methods of the invention. In one embodiment, the kit further comprises reagents, equipment (test tubes, reaction vessels, needles, syringes, etc.). The instructions provided in a kit according to the invention may be directed to suitable operational parameters in the form of a label or a separate insert. Optionally, the kit may further comprise a standard or control information so that the test sample can be compared with the control information standard to determine whether a consistent result is achieved.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Age-Associated Insulin Resistance was Driven by fTregs

The young, lean state is associated with insulin sensitivity, however both aging and obesity can lead to the development of insulin resistance (FIG. 1A). To distinguish key immune cell types that drive age-versus obesity-associated insulin resistance, the immune cell components of adipose depots were quantitatively profiled using a flow cytometry approach termed adipo-immune profiling (AIP) (FIG.

Figure 1B:
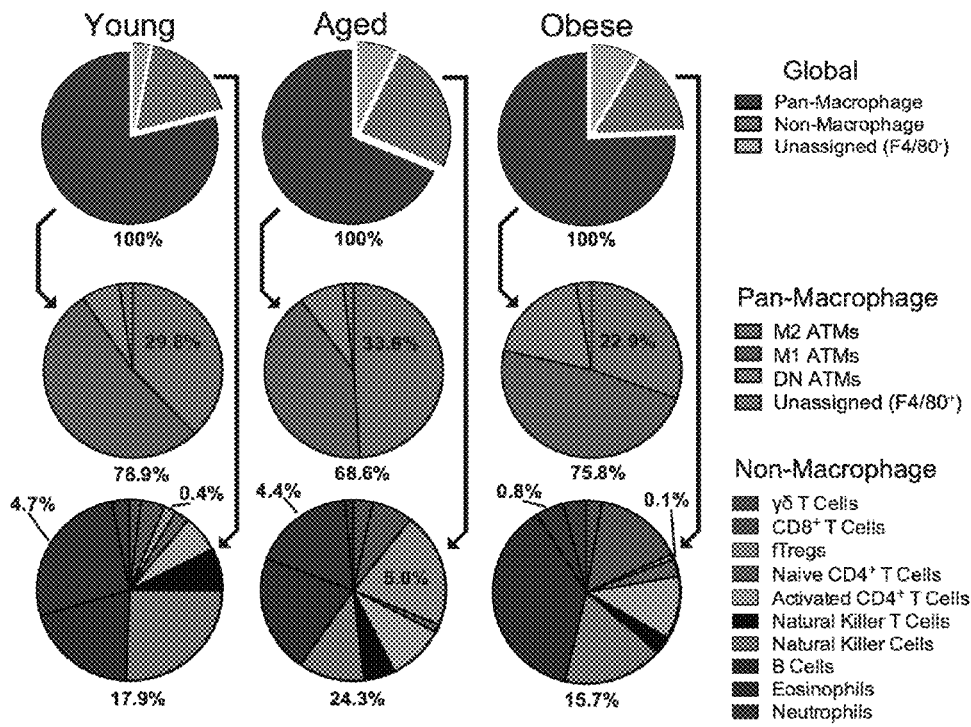
Figure 1C:
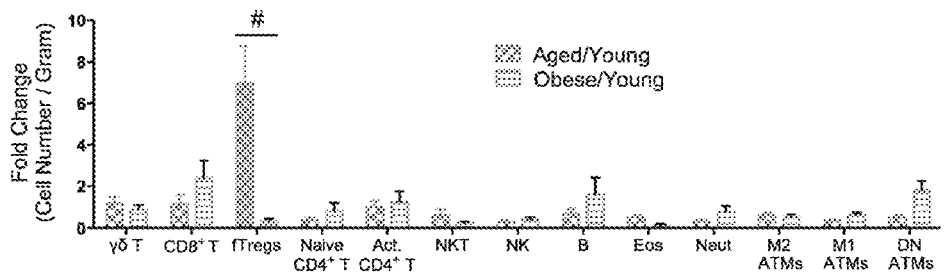
Figure 2A:
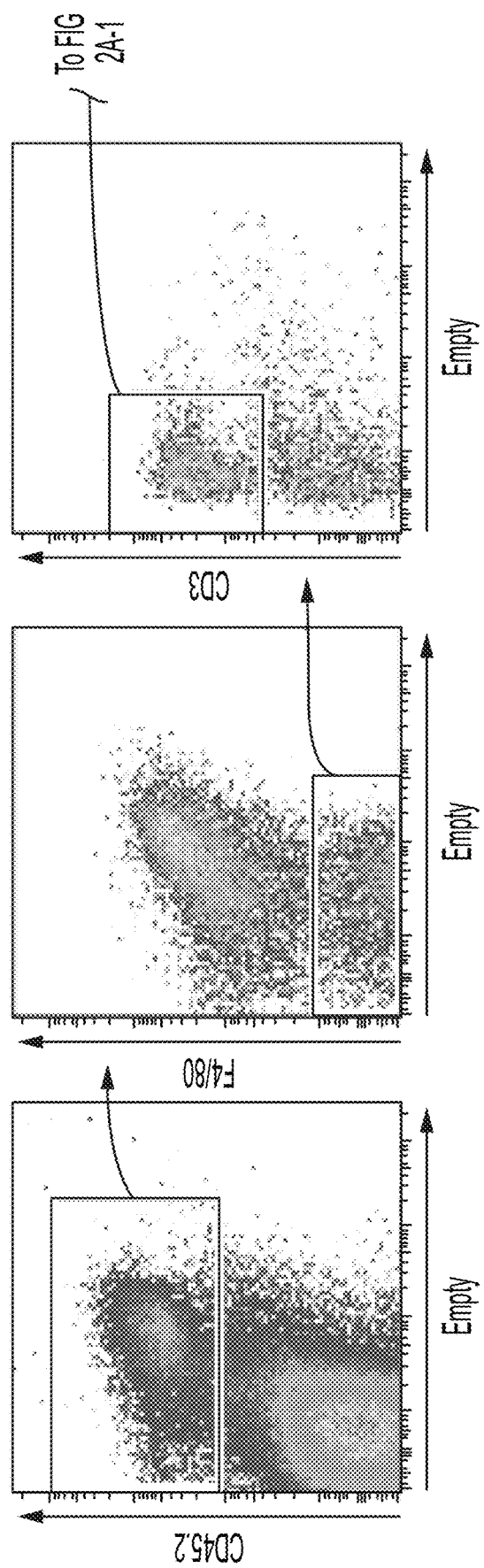
FIGS. 2A-2C are 12 scatter plots showing selected gating strategies used to generate adipoImmune Profiles (AIPs)—AdipoImmune Profiles were generated through the use of several distinct antibody cocktails.
Figures 1, 2A:
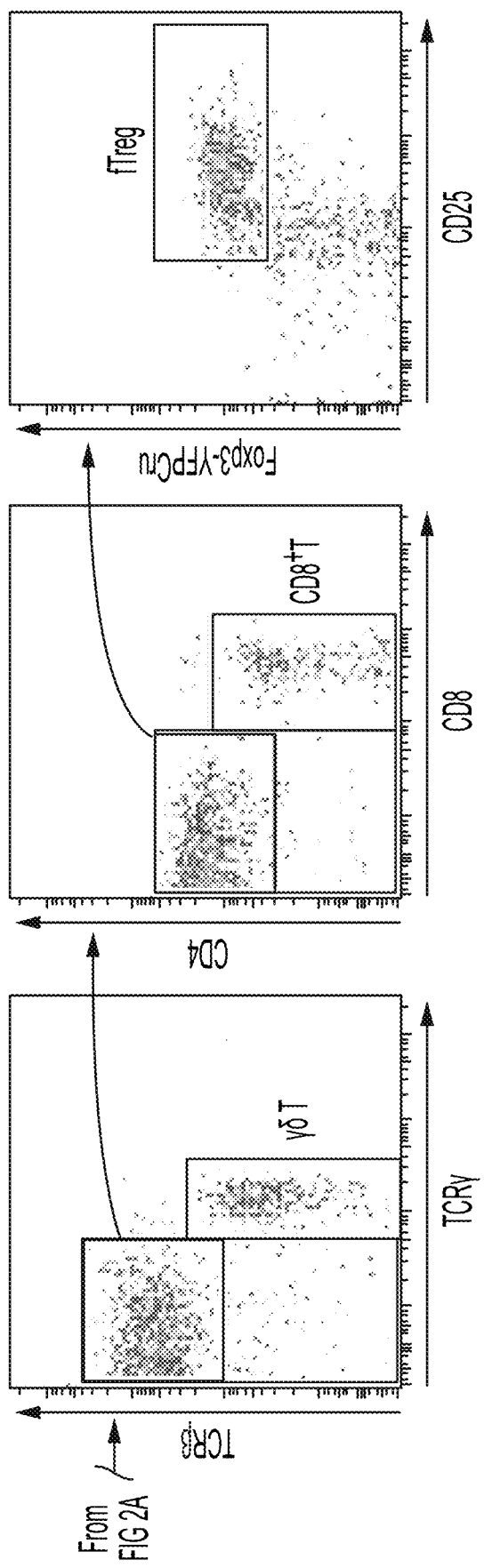
Figure 2B:
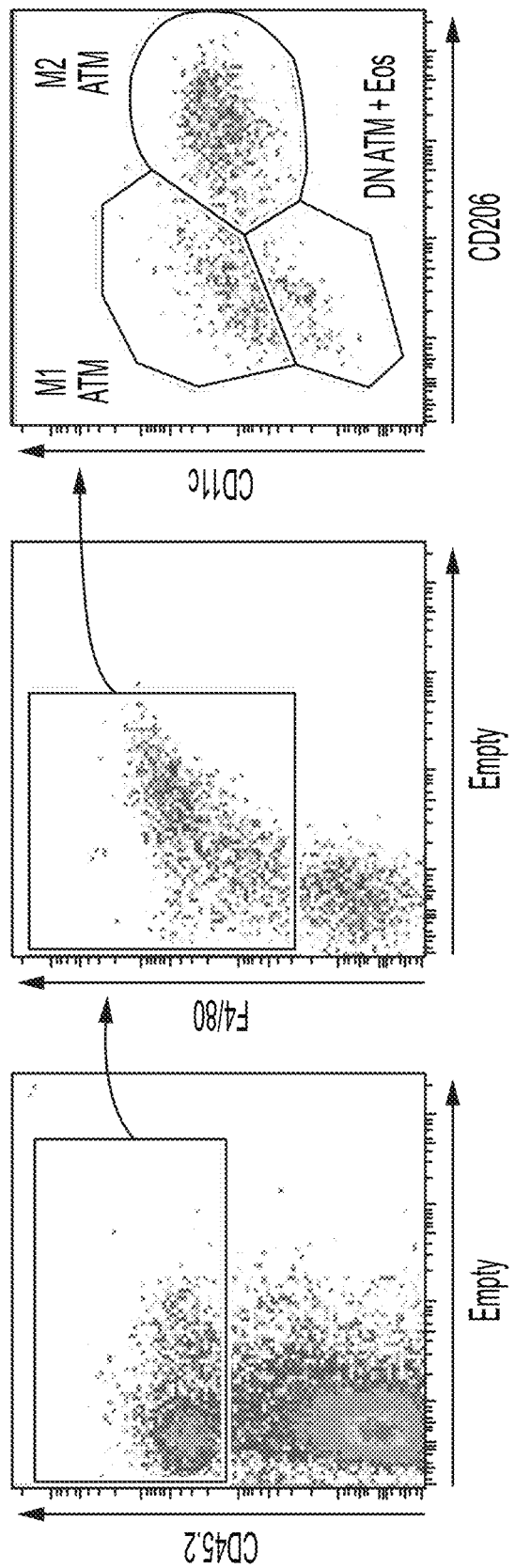
Figure 2C:
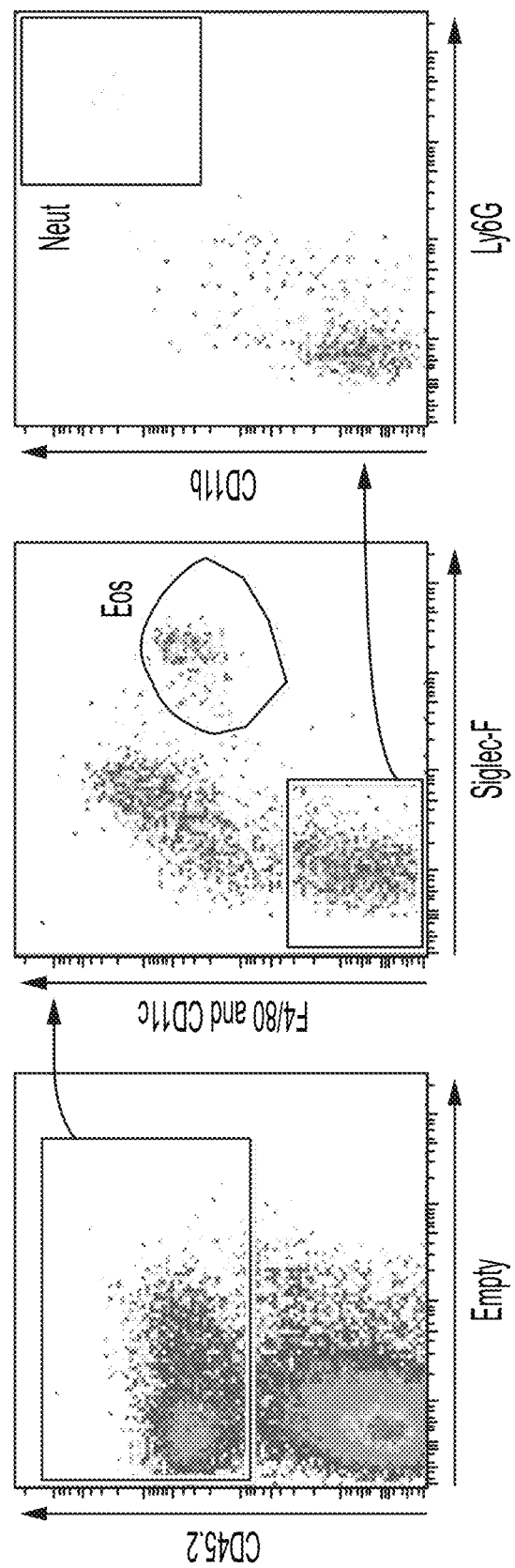

2A-FIG. 2C, Table 1). In contrast to the decrease in anti-inflammatory M2 adipose tissue macrophages (ATMs) and eosinophils observed in obesity-driven insulin resistance, AIP revealed that these cell populations were largely unperturbed in visceral adipose tissue from aged mice (M2 ATMs—aged: 33.6±3.8%, young: 29.8±4.1%, obese: 22.9±6.3%; eosinophils—aged: 4.4%±1.6%, young: 4.7%±0.7%, obese: 0.8%±1.0%, FIG. 1B). Rather, the relative portion of the non-macrophage compartment was significantly increased in aged compared to young or obese mice (aged: 24.3±4.6%, young: 17.9±2.8%, obese 15.7±3.8%, FIG. 1B), which was largely attributable to a ~13.5 fold expansion in the fat-resident regulatory T cell (fTreg) population (aged: 5.0±1.2%, young: 0.4±0.1%, obese: 0.1±0.1%, FIG. 1B and FIG. 1C). These varying AIP signatures of adipose tissue indicated that distinct patho-physiologic processes drive age- and obesity-associated insulin resistance and implicated fTregs as potential drivers of age-associated insulin resistance.

TABLE 1

Antibodies used to molecularly identify the given immune cell type.

| Immune Cell Type | Molecular Identification Scheme |
|---|---|
| TCRγδ | CD45.2+ F4/80− CD3+ TCRb− TCRγ+ |
| CD8+ | CD45.2+ F4/80− CD3+ TCRb+ CD4− CD8+ |
| Treg CD4+ | CD45.2+ CD4+ CD25+ Foxp3+ |
| Naïve CD4+ | CD45.2+ CD4+ CD25− Foxp3− CD62L$^{hi}$ CD44$^{lo}$ |
| Activated CD4+ | CD45.2+ CD4+ CD25− Foxp3− CD62L$^{lo}$ CD44$^{hi}$ |
| NKT | CD45.2+ NK1.1+ TCRb+ |
| NK | CD45.2+ NK1.1+ TCRb− |
| B | CD45.2+ NK1.1− CD19+ |
| Eosinophil | CD45.2+ F4/80+ Siglec-F+ |
| Neutrophil | CD45.2+ F4/80− Cd11c− CD11b+ Ly6G+ |
| M2 ATM | CD45.2+ F4/80+ Cd11c$^{med}$ CD206+ |
| M1 ATM | CD45.2+ F4/80+ Cd11c$^{hi}$ CD206− |
| DN (Double-negative) ATM | CD45.2+ F4/80+ Cd11c− CD206− |

Figure 3A:
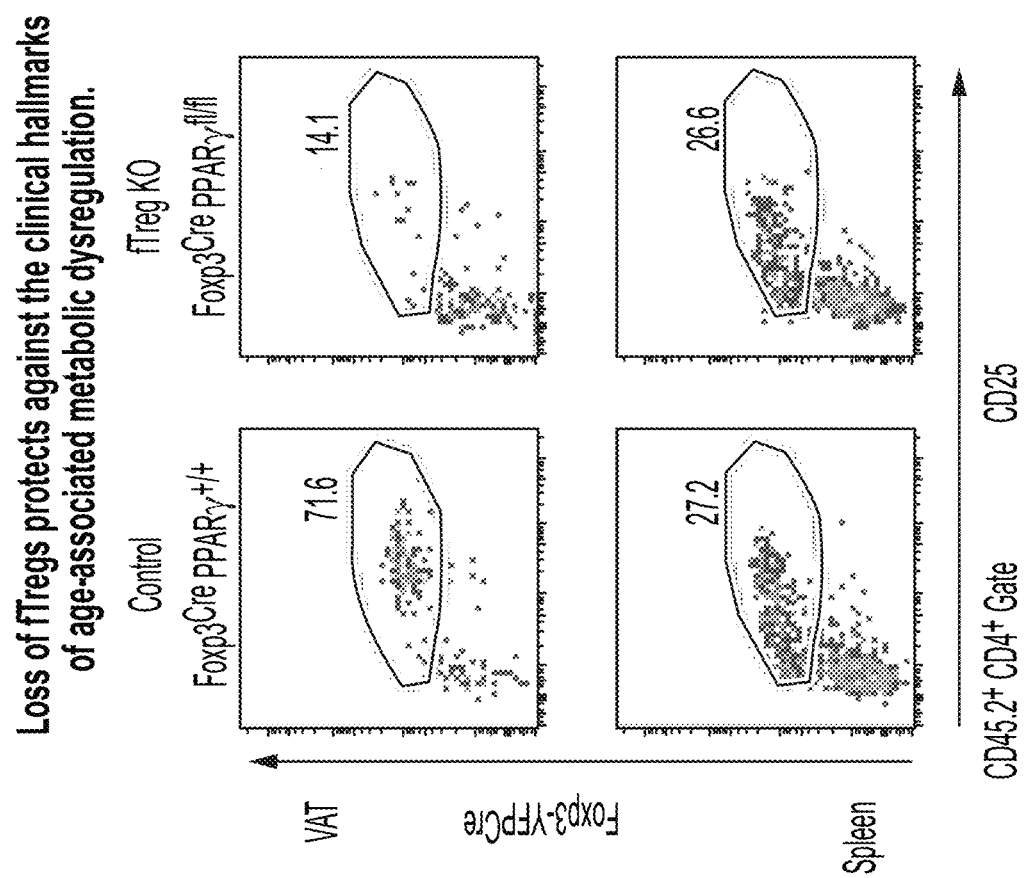
Figures 4A, 4B:
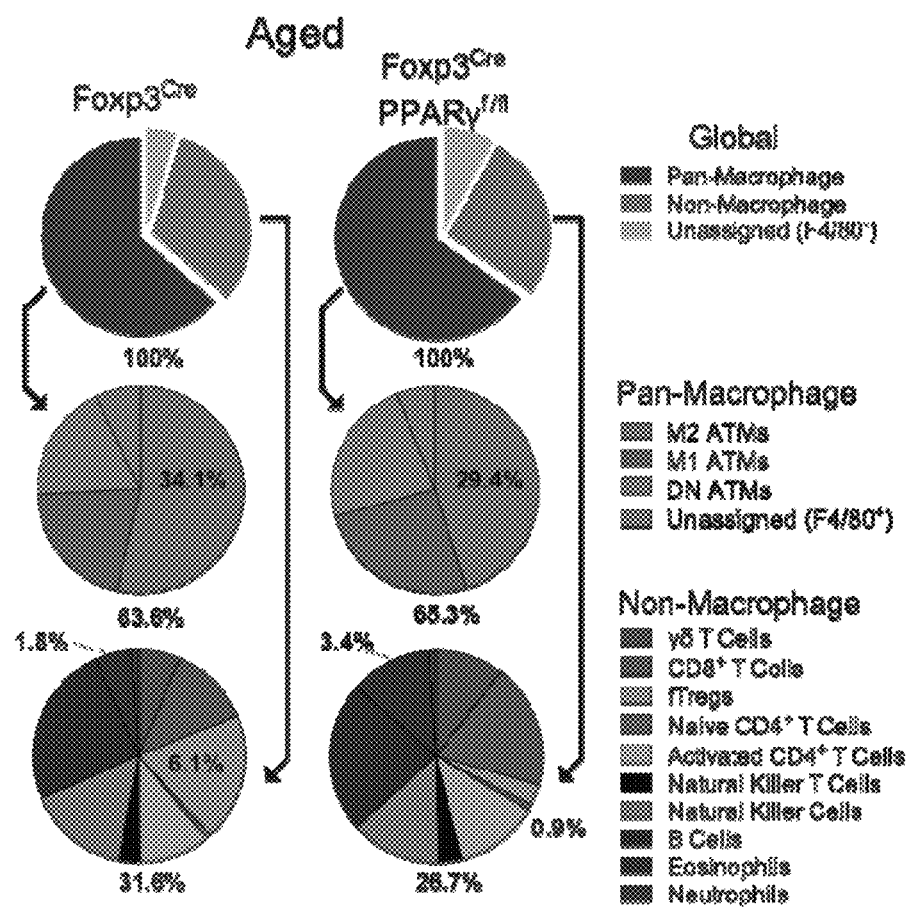
FIGS. 4A-4B are pie charts and a bar graph showing visceral adipose tissue (VAT) adipoImmune Profiles (AIPs) of aged fTreg KO and control mice.
Figure 5A:
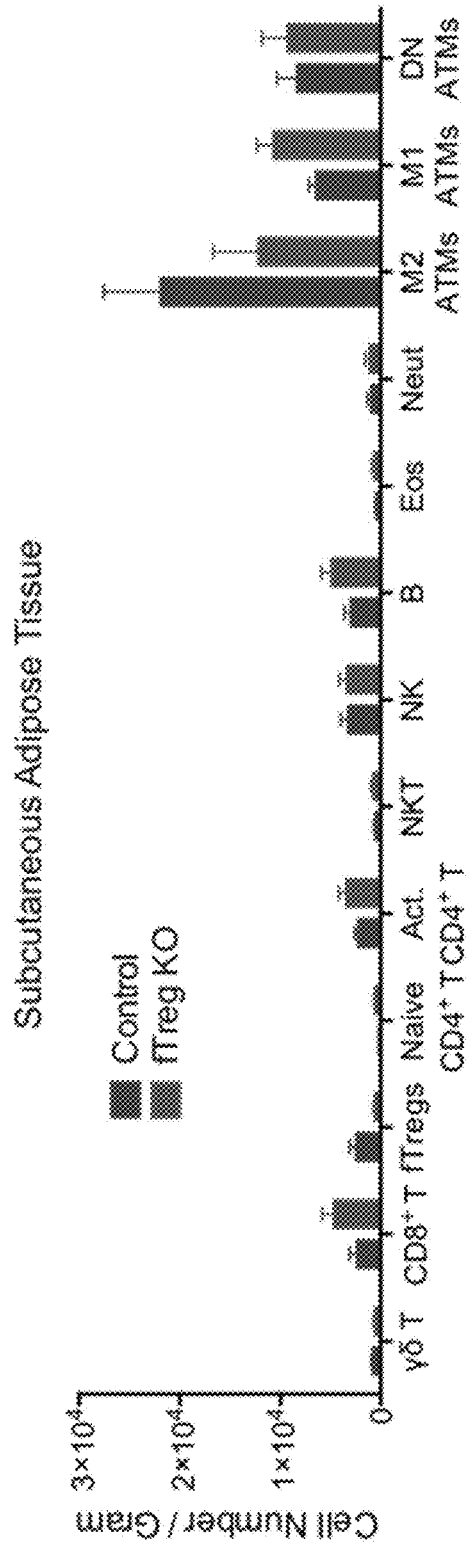
FIGS. 5A-5B are two bar graphs showing subcutaneous adipose tissue (SAT) adipoImmune and spleen immune profiles of fTreg KO and control mice.
Figure 5B:
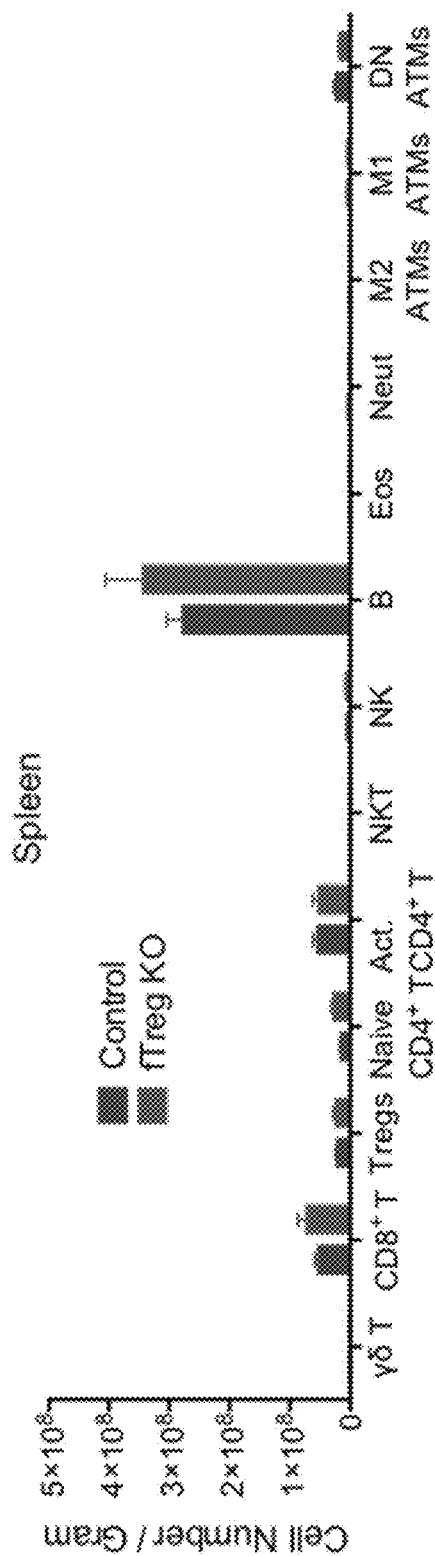
Figure 6B:
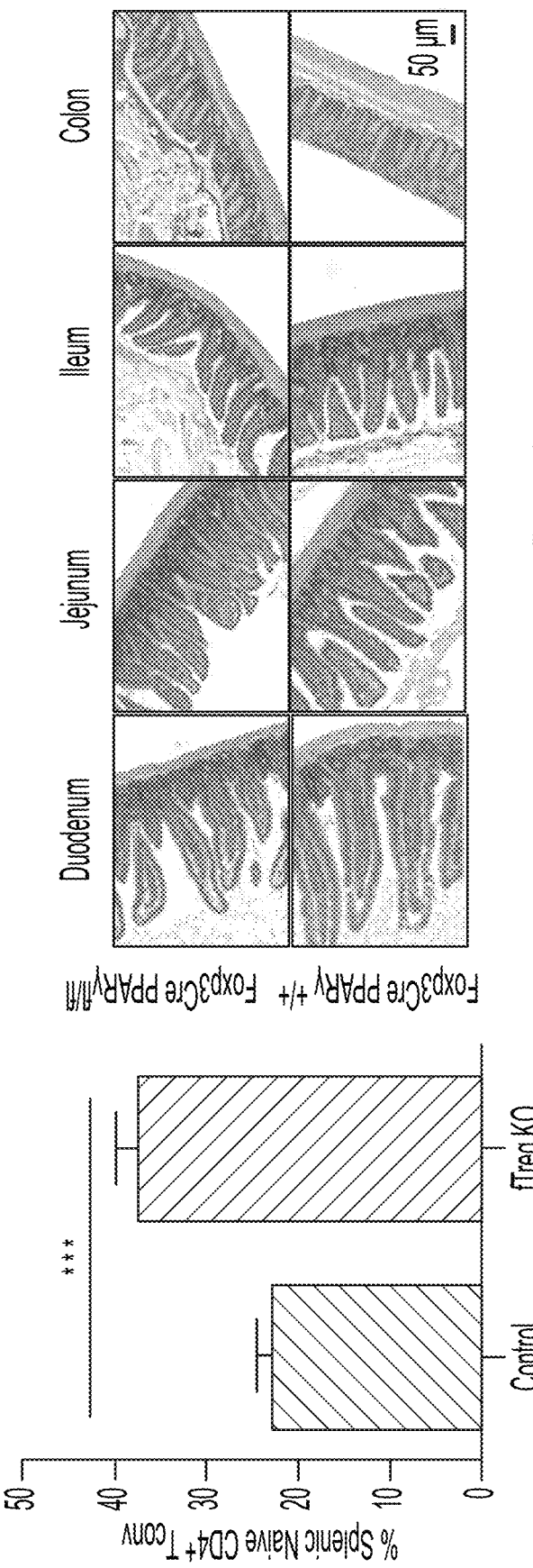
FIGS. 6A-6D are bar graphs and histological images showing that aged fTreg KO mice did not show signs of systemic autoimmunity or breakdown in peripheral tolerance.
Figure 6A:
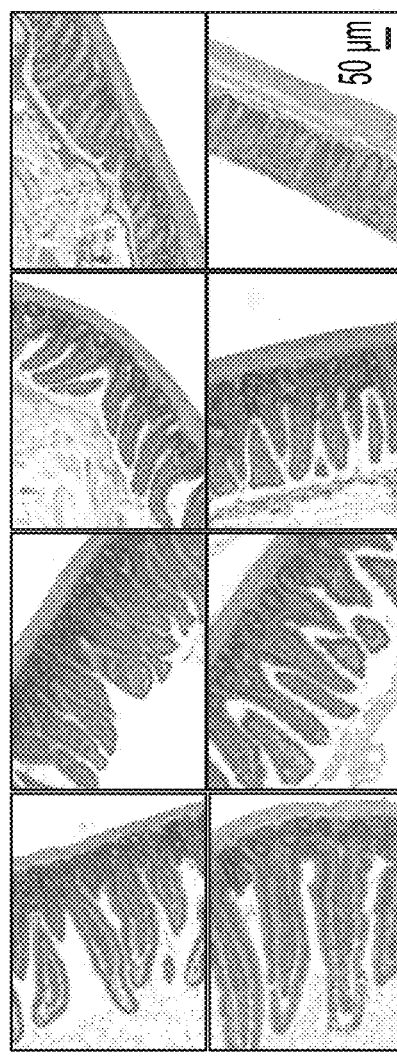
Figure 6C:
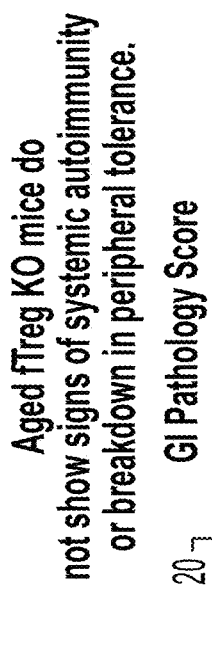
Figure 6D:
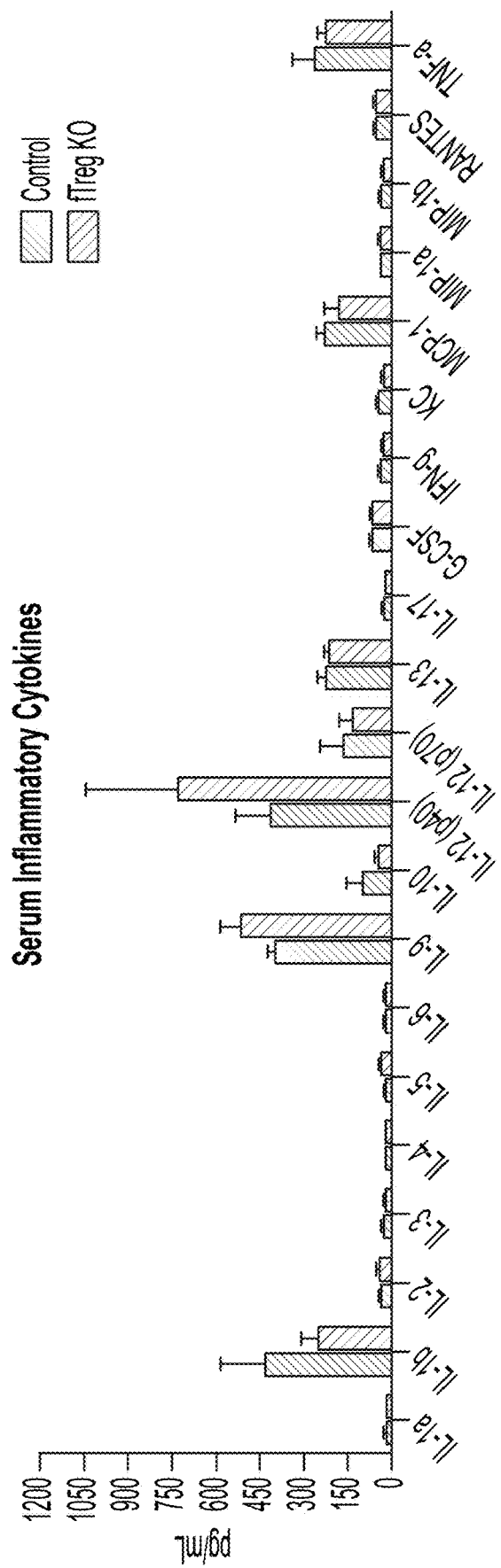

Example 2: AdipoImmune Profiles of Control and fTreg KO Mice Looked Nearly Identical To explore the role of fat-resident regulatory T cells (fTregs) in age-associated insulin resistance, Foxp3$^{Cre}$ Pparg$^{fl/fl}$ mice were utilized in which Tregs were selectively depleted from visceral adipose tissue (fTreg KO mice, FIG. 3A, FIG. 4A and FIG. 4B, Cipoletta et al., Nature. doi: 10.1038/nature11132, 2012) without significantly altering the immune profiles of subcutaneous adipose tissue or spleen (FIG. 5A and FIG. 5B). Importantly, the visceral adipose tissue-specific loss of fTregs did not elicit any overt signs of systemic inflammation generally associated with Treg dysfunction. Aged fTreg KO mice had normal-sized spleens and increased CD62L$^{hi}$ CD44$^{lo}$ naïve CD4$^+$ T cell populations compared to wild-type controls (FIG. 3C, FIG. 6A). The normal intestinal histology provided additional evidence that the Treg population was not perturbed (FIG. 6B and FIG. 6C). Furthermore, no differences were observed in the levels of inflammatory cytokines, including TNFα, IL1b, IL6, IFNγ, and IL17, in the serum of aged fTreg KO compared to control mice (FIG. 6D).

Figure 3H:
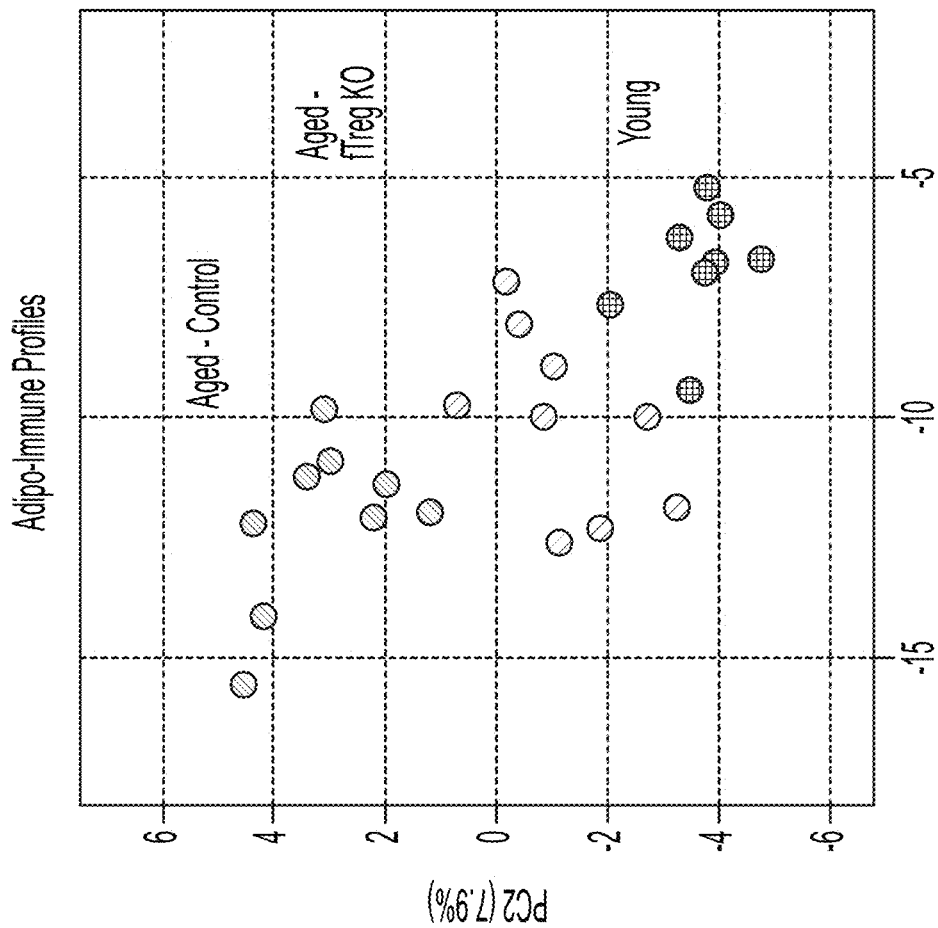
Figure 3G:
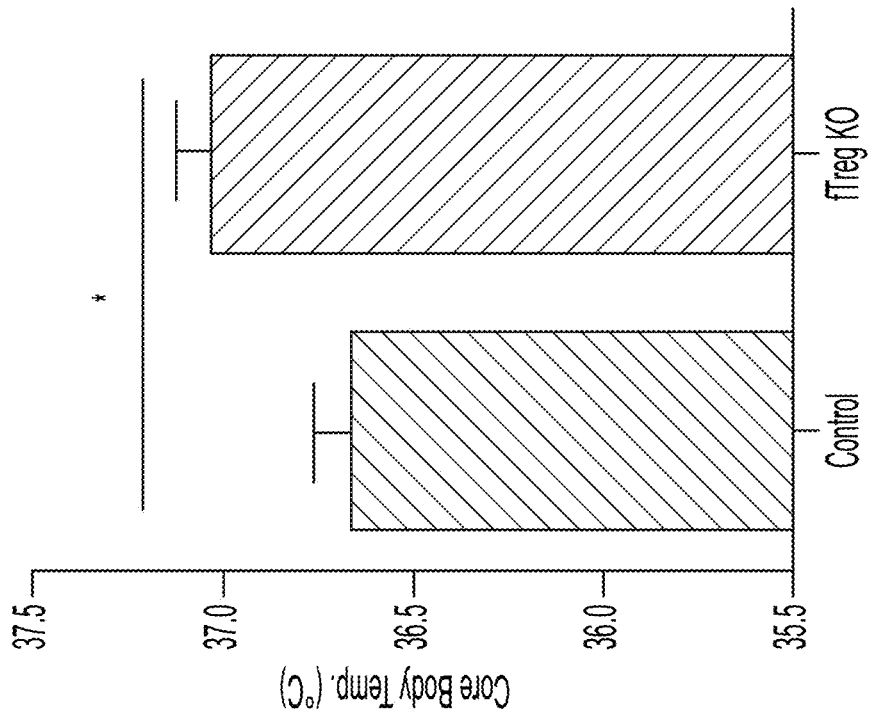

Example 3: fTreg KO Mice were Protected Against Age-Associated, but not Obesity-Associated Insulin Resistance Importantly, the selective loss of fTregs attenuated many of the hallmarks of age-associated metabolic dysregulation. They weighed less than control mice and were leaner (decreased visceral adipose tissue and subcutaneous adipose tissue adiposity) despite increased food consumption (FIGS. 3B-3D). In addition, the respiratory exchange ratio (RER, FIG. 3E), oxygen consumption (FIG. 3F), and core body temperature (FIG. 3G) were increased in aged fTreg KO mice relative to control mice. These marked improvements indicated that the age-associated metabolic phenotype was closely linked with visceral adipose tissue immune responses, and that in the aged setting, a reduction in fTreg numbers might be protective. Indeed, the adipo-immune profilings of aged fTreg KO mice were shifted towards those of young mice, as visualized by principal component analysis (FIG. 3H).

Figures 7A, 7B, 7C:
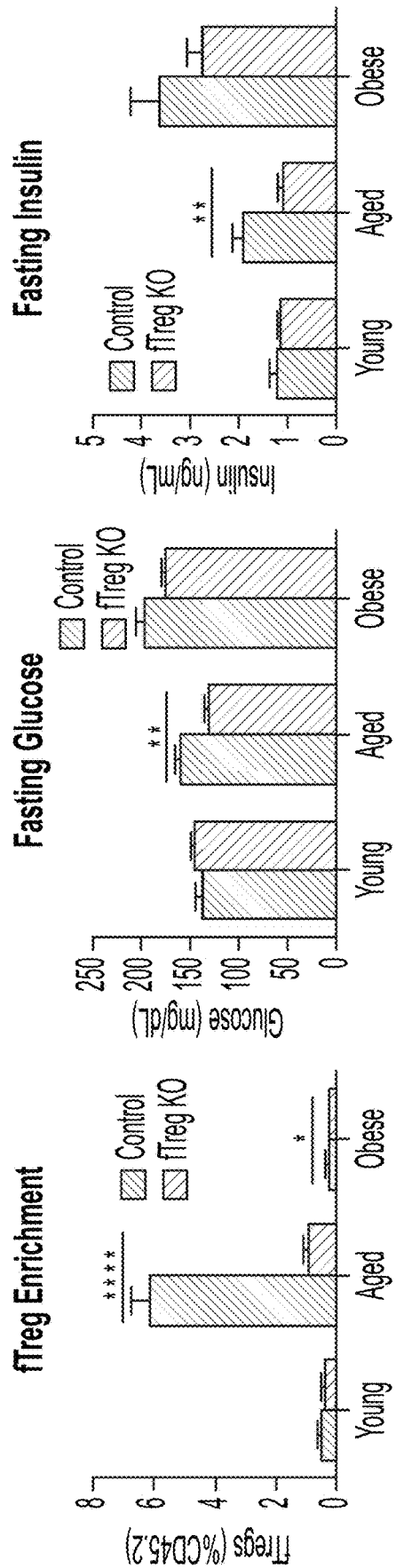
FIGS. 7A-7P are linear and bar graphs and histological images showing that loss of fTregs protected against the clinical hallmarks of age-associated insulin resistance.
FIG. 7B and FIG. 7C are two bar graphs showing fasting serum glucose (FIG. 7B) and insulin levels (FIG. 7C) in control and fTreg KO mice in young (control n=9; fTreg KO n=9), aged (36 weeks old, control n=9; fTreg KO n=11), and obese mice (control n=10; fTreg KO n=10).
Figure 7D:
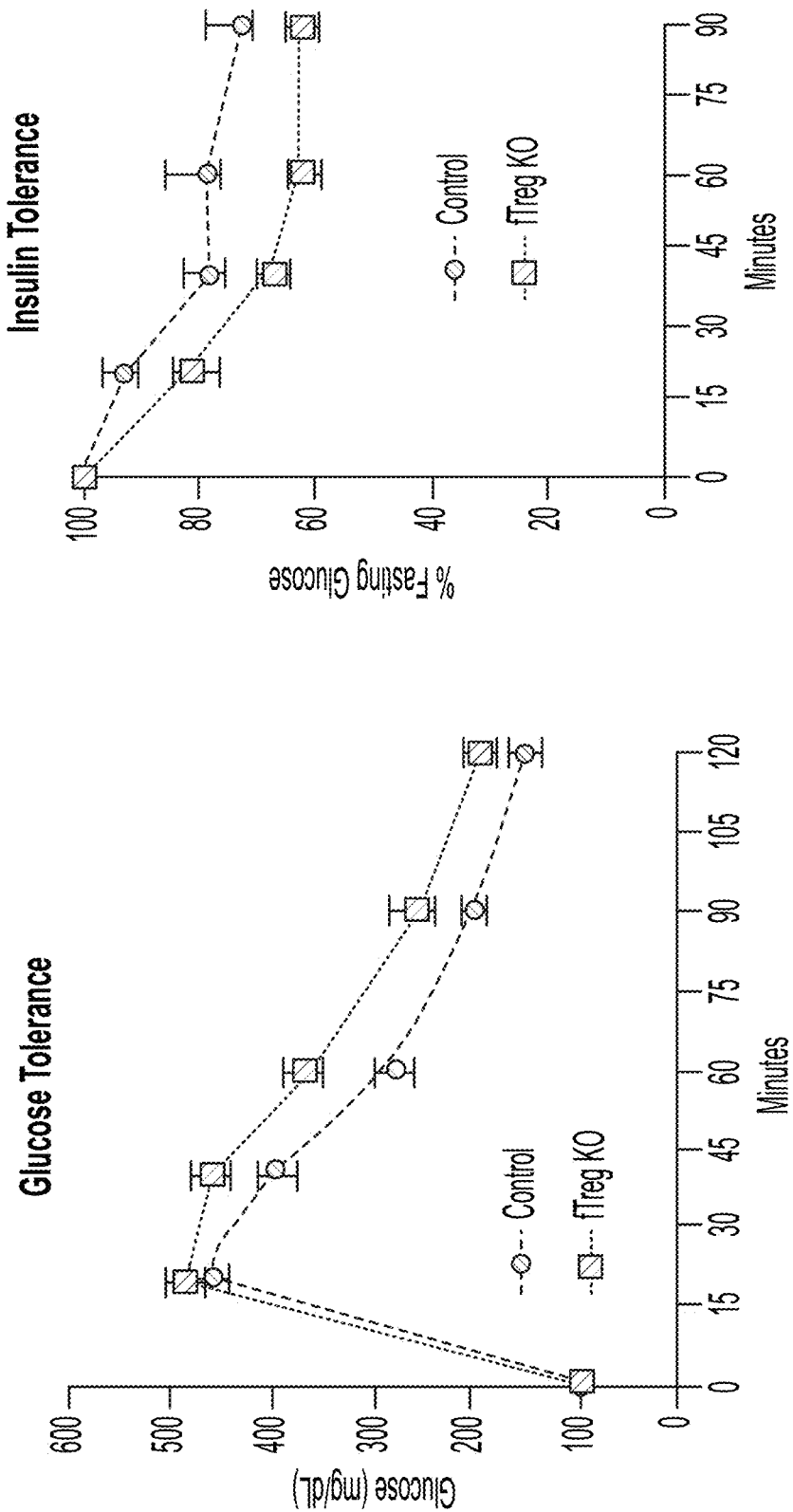
FIGS. 7D-7F are six linear graphs showing glucose tolerance and insulin tolerance tests of control and fTreg KO mice at young (FIG. 7D, 12 weeks, control n=8; fTreg KO n=8), aged (FIG. 7E, 36-37 weeks, control n=8; fTreg KO n=9), and obese mice (FIG. 7F, control n=9; fTreg KO n=10).
Figure 7E:
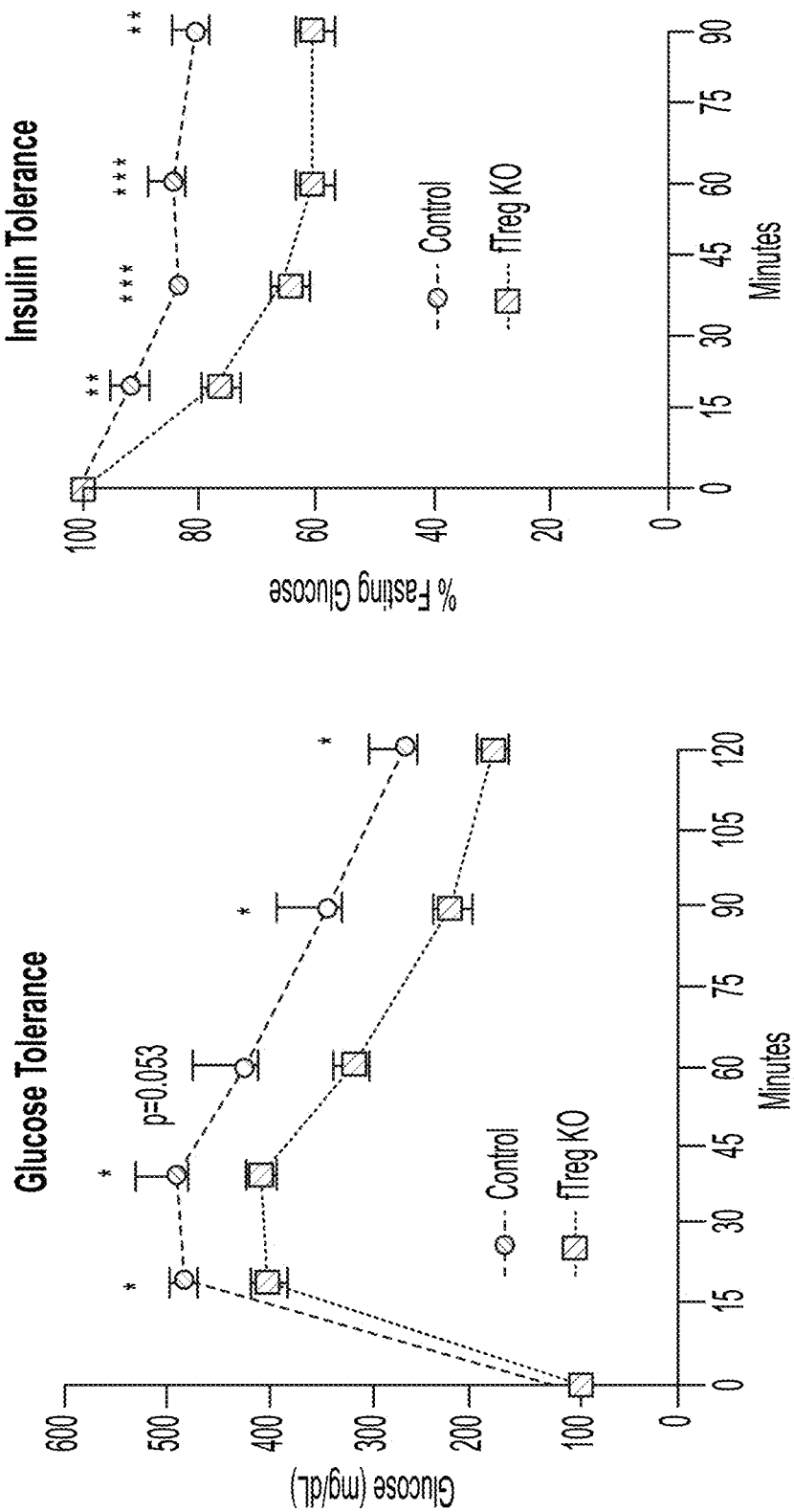
Figure 7F:
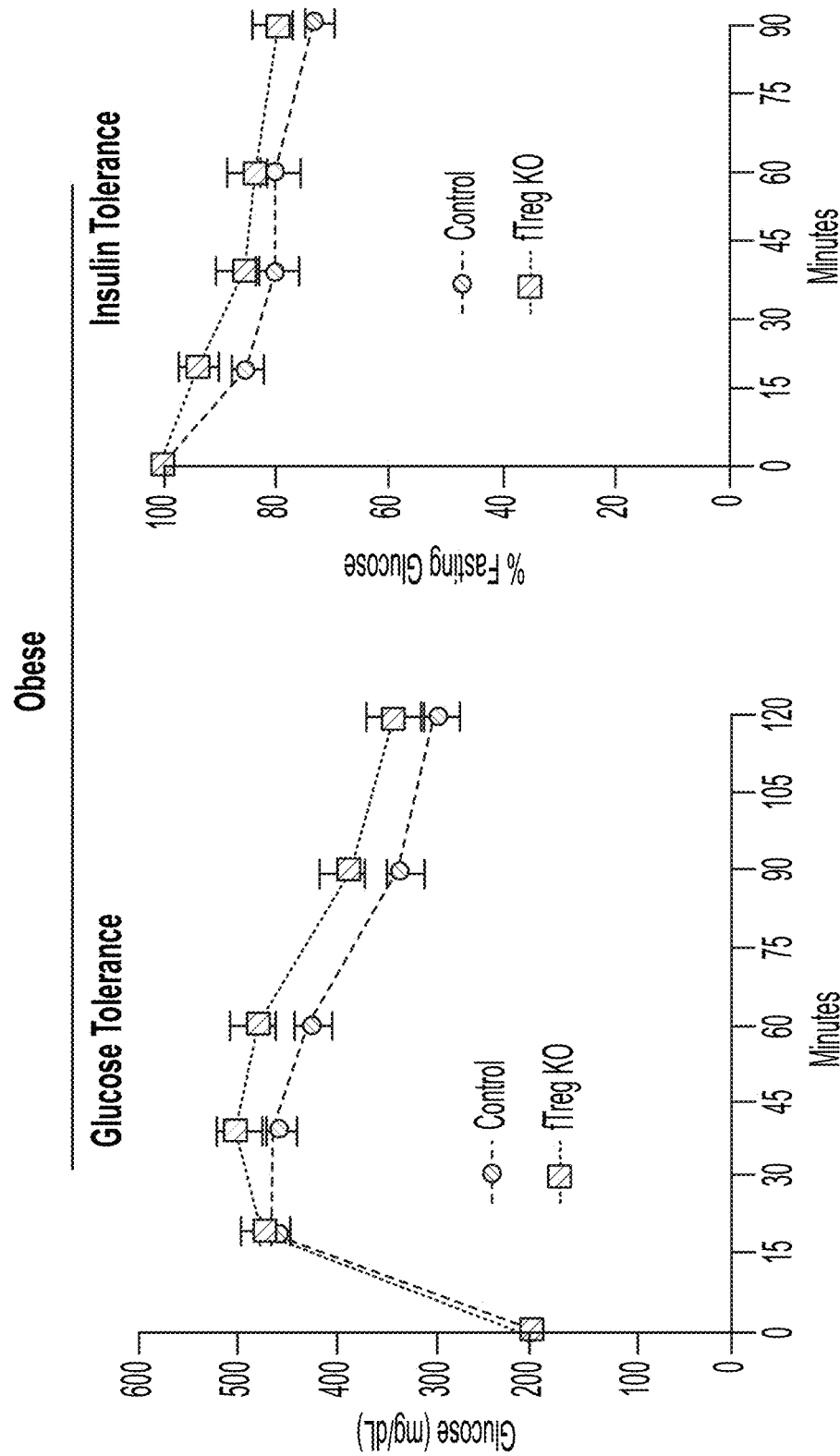
Figure 8:
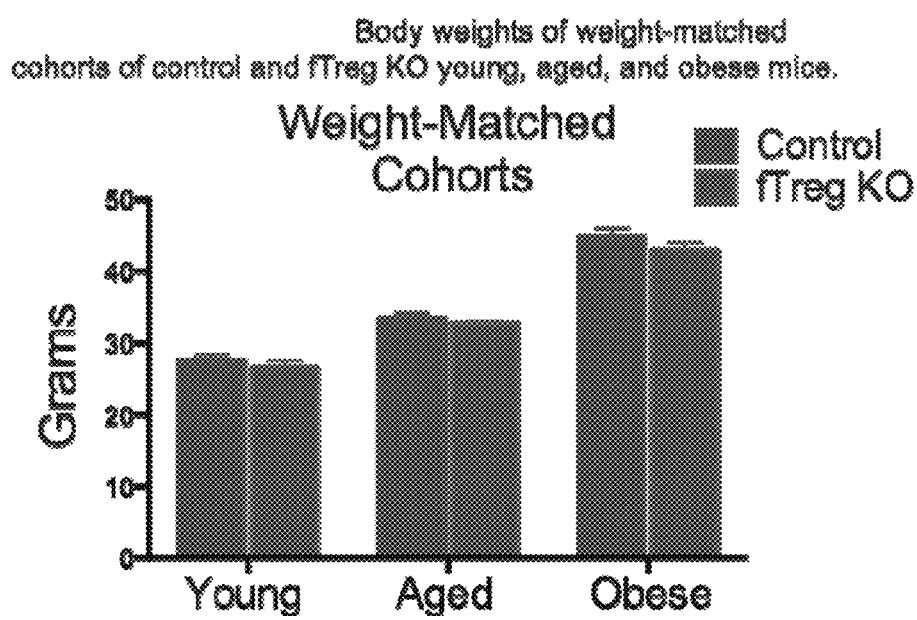
FIG. 8 is a bar graph comparing body weights of weight-matched cohorts of control and fTreg KO young, aged, and obese mice. Body weights of fTreg KO and control male mice used in weight-matched metabolic studies in young (12 week old; control n=9; fTreg KO n=9), aged (36 week old; control, n=9 mice; fTreg KO, n=11 mice), and obese (diet-induced obese (DIO), 12 weeks of high fat diet (HFD) starting at 12 weeks old; control n=10; fTreg KO n=10) settings.
Figure 9A:
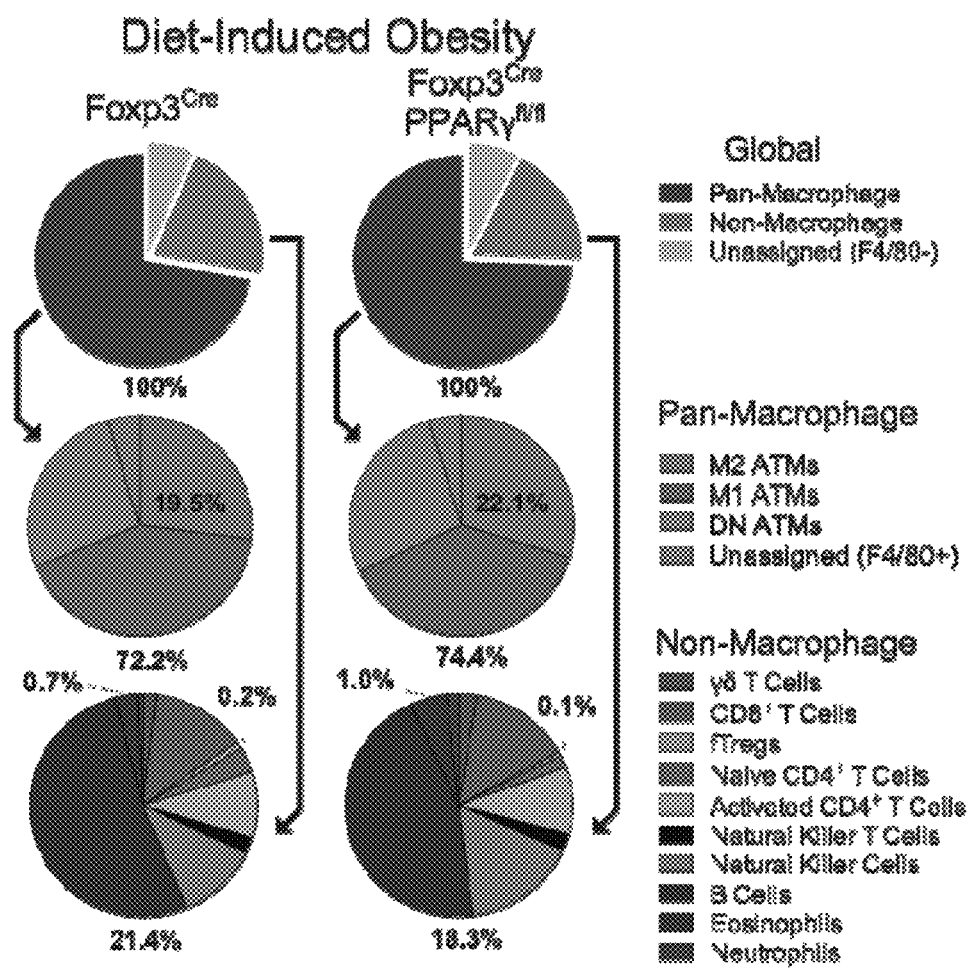
FIGS. 9A-9B are pie charts and a bar graph showing visceral adipose tissue (VAT) adipoImmune profiles of obese fTreg KO and control mice.
Figure 9B:
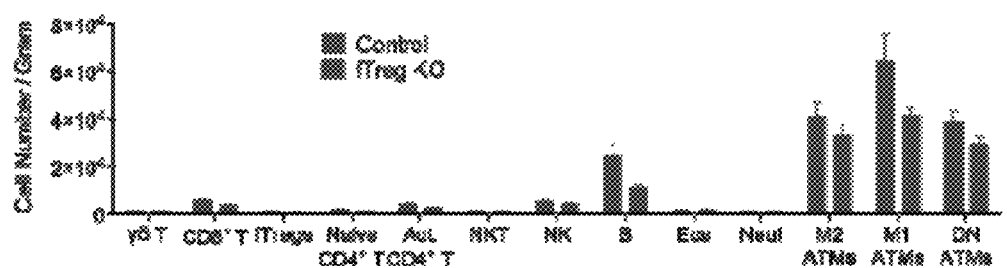

The fTreg KO phenotype was most pronounced in aged mice, though a reduction in fTreg levels was also seen in obese fTreg KO mice (FIG. 7A). Consistent with the notion that fTregs are drivers of age-associated metabolic dysregulation, fasting serum glucose and insulin levels were significantly reduced in aged fTreg KO mice (FIG. 7B and FIG. 7C and FIG. 8). Furthermore, aged fTreg KO mice displayed smaller glucose excursions during glucose tolerance tests and increased sensitivity during insulin tolerance tests compared to weight-matched control mice (FIG. 7E). Notably, these improvements in glucose homeostasis were observed only in aged mice; no significant differences were seen in young or obese fTreg KO mice (FIG. 7D and FIG. 7F), which was consistent with the largely unchanged adipo-immune profiling (AIP) of obese fTreg KO mice (FIG. 9A and FIG. 9B).

Figures 7I, 7J, 7K:
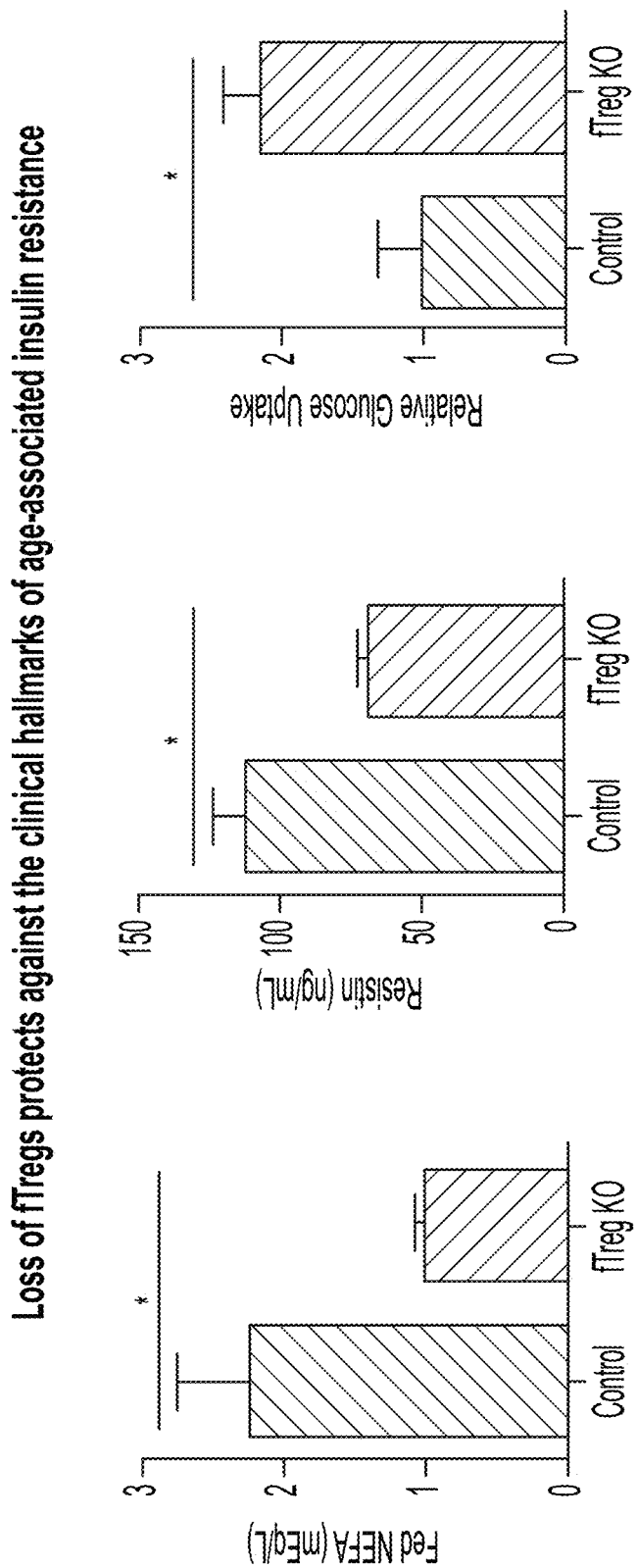
FIG. 7I is a bar graph comparing ad libitum fed serum non-esterified fatty acid (NEFA) levels in aged control (n=9) and fTreg KO mice (n=10).
FIG. 7J is a bar graph comparing serum resistin levels in ~14 month old fasted control and fTreg KO mice (n=4 pooled samples (2 mice per sample) per group).
FIG. 7K is a bar graph comparing post-prandial glucose uptake in visceral adipose tissue of aged control (n=5) and fTreg KO mice (n=4). FIG.
Figures 7L, 7M:
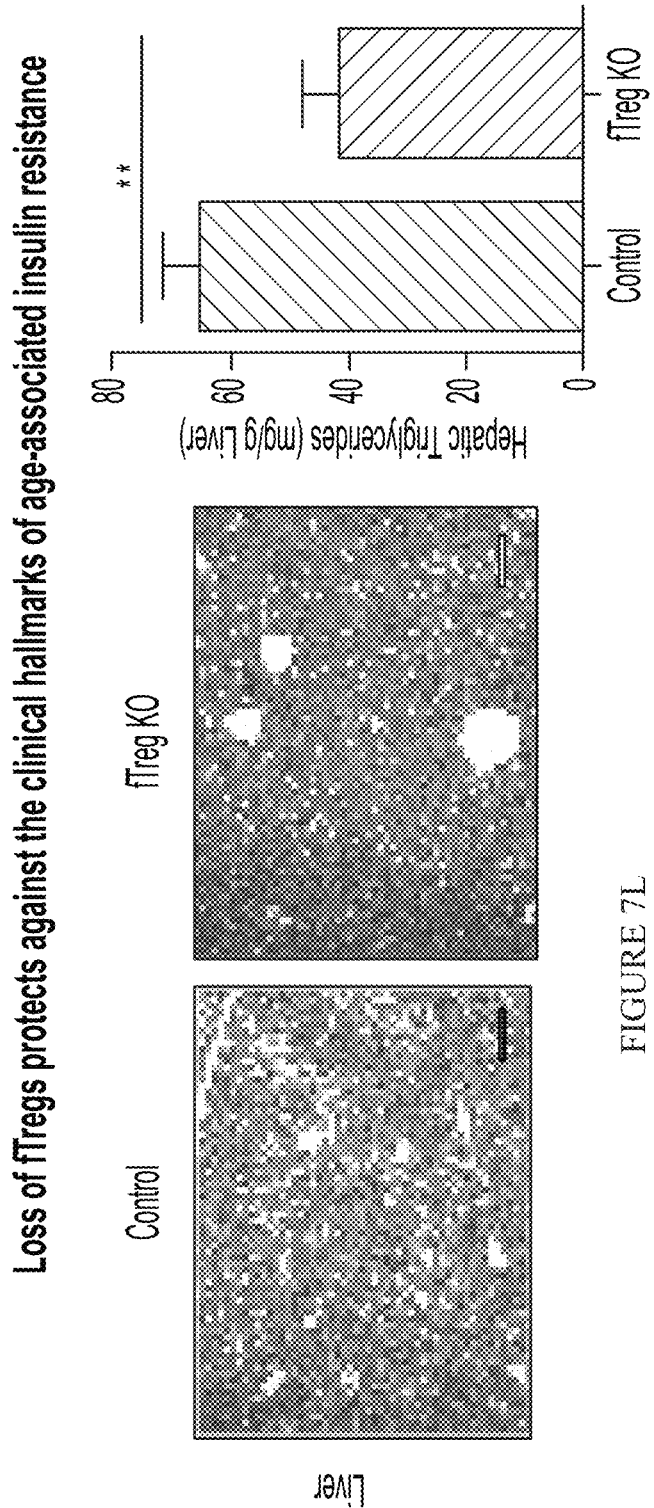
FIG. 7M is a bar graph comparing hepatic triglyceride levels in ~14 month old control (n=5) and fTreg KO mice (n=3).
Figures 7N, 7O, 7P:
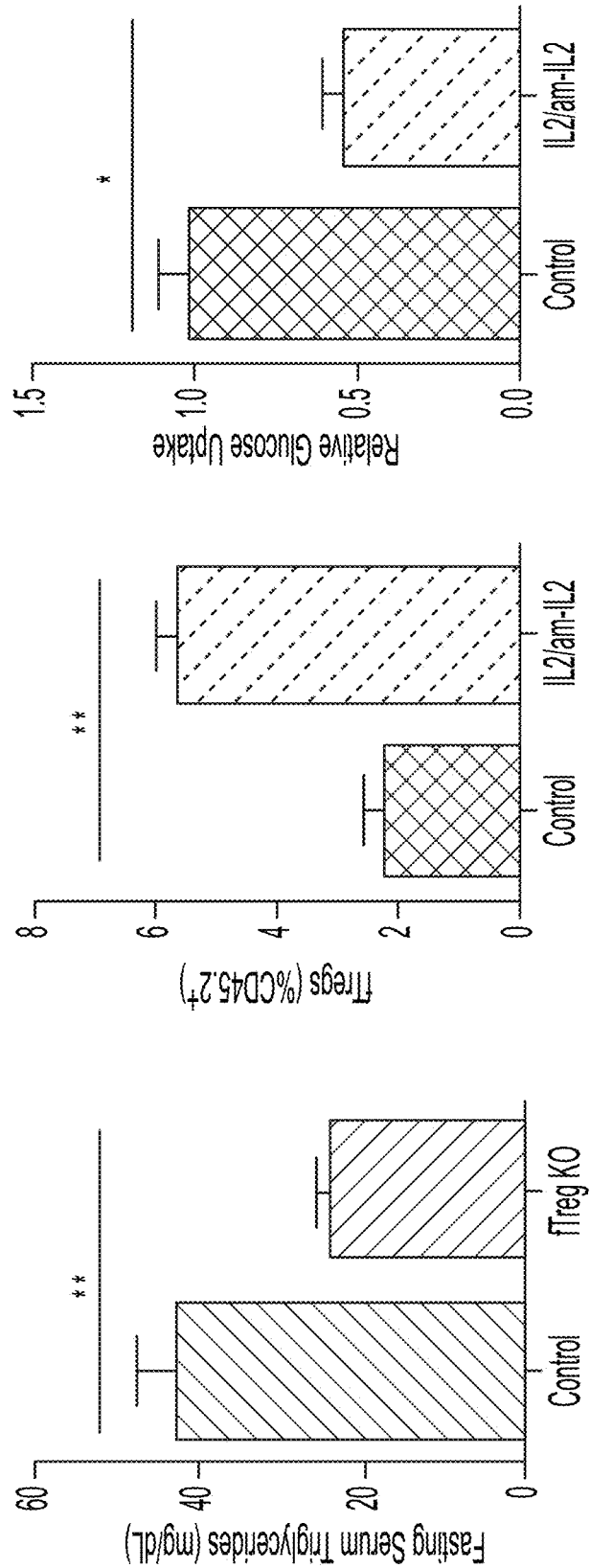
FIG. 7N is a bar graph showing fasting serum triglycerides in ~14 month old control (n=9) and fTreg KO mice (n=10).
FIG. 7O is a bar graph showing fTregs, expressed as % of total $CD45.2^+$ cells, in control and IL2/anti-IL2 treated mice (n=3 mice per group).
Figure 10:
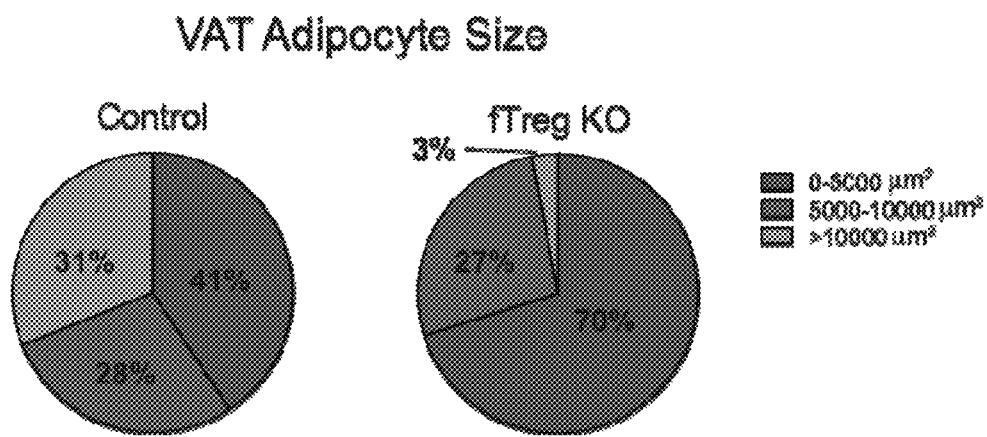
FIG. 10 includes two pie charts showing frequency of small, medium, and large adipocytes in visceral adipose tissue (VAT) of aged control and fTreg KO mice. Frequency of small (0-5000 μm$^2$), medium (5000-10,000 μm$^2$), and large (>10,000 μm$^2$) adipocytes in VAT of aged control and fTreg KO mice (n=3 mice per group, 850 adipocytes counted from control mice, 269 adipocytes counted from fTreg KO adipose).

Example 4: Hallmarks of Insulin Resistance were Attenuated in fTreg KO Mice Compared to Age-Matched Controls Histologically, aged fat-resident regulatory T cell (fTreg) KO visceral adipose tissue depots appeared similar to control mice, and inflammatory processes such as crowning were observed at comparable frequencies (FIG. 7G). However, adipocytes from aged fTreg KO mice were smaller than those in control mice (fTreg KO 70%<5000 mm$^2$, control ~41%<5000 mm$^2$, FIG. 7H and FIG. 10), and serum non-esterified free fatty acid (NEFA) levels were reduced to almost half those of control mice; both indicators of improved insulin sensitivity (FIG. 7I). In addition, circulating levels of the adipokine resistin, which positively correlates with murine insulin resistance, were reduced in the aged fTreg KO mice (FIG. 7J). Furthermore, aged fTreg KO mice presented with decreased hepatic steatosis, as determined histologically and by decreased fasting hepatic and serum triglyceride content (FIGS. 7L-7N). In combination, these findings indicated that the loss of fTregs in adipose tissue alleviated many of the indications of age-associated insulin resistance in mice, a primary clinical manifestation of metabolic aging.

To more directly associate fTregs with age-associated insulin resistance, basal glucose uptake was measured in adipose tissue ex vivo. Notably, visceral adipose tissue from fTreg KO mice took up almost twice the amount of glucose as control tissue (FIG. 7K). Conversely, expansion of fTregs in wild-type mice via treatment with IL-2/IL-2 mAb complex treatment abrogated basal glucose uptake in visceral adipose tissue by ~50% (FIG. 7O and FIG. 7P). This inverse correlation between fTreg numbers and glucose uptake in adipose tissue supported a causal association between fTregs and insulin resistance during aging.

Figure 11A:
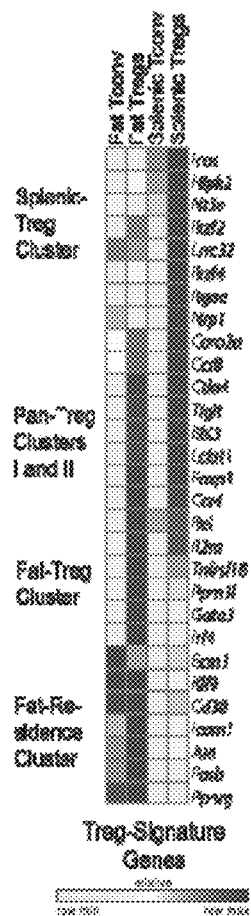
FIGS. 11A-11B depict an RNA-Seq analysis heat map and a scatter plot of fTreg gene expression.
Figure 11B:
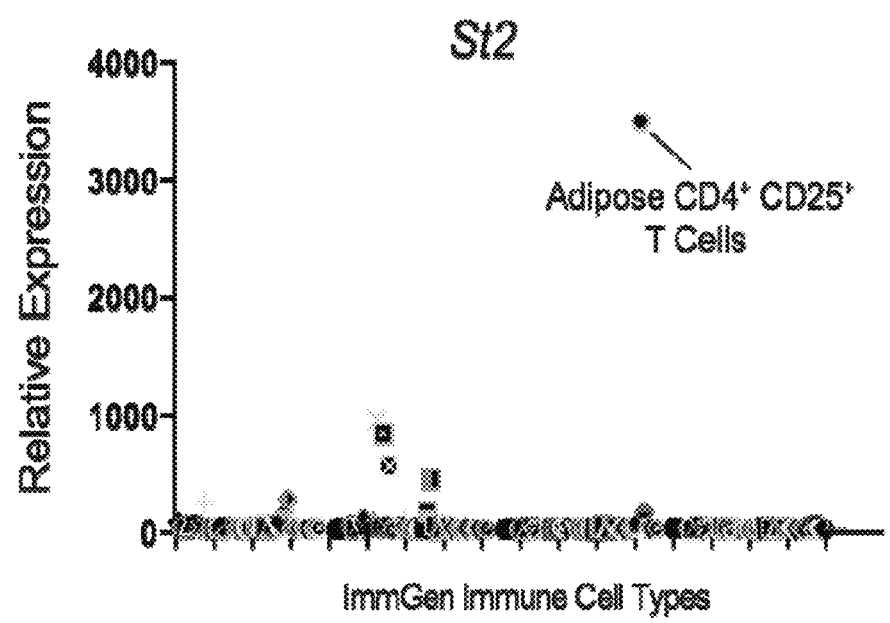
Figure 12A:
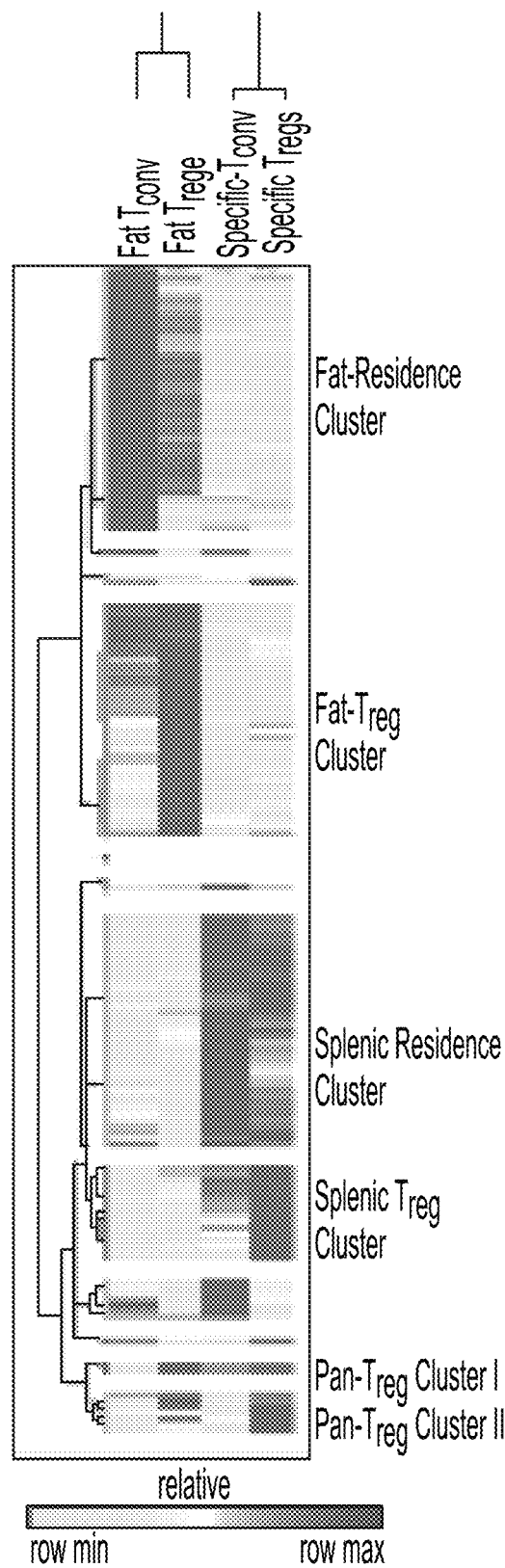
FIGS. 12A-12L are heat maps and graphs showing that fTreg depletion improved adipose glucose uptake.
Figure 12B:
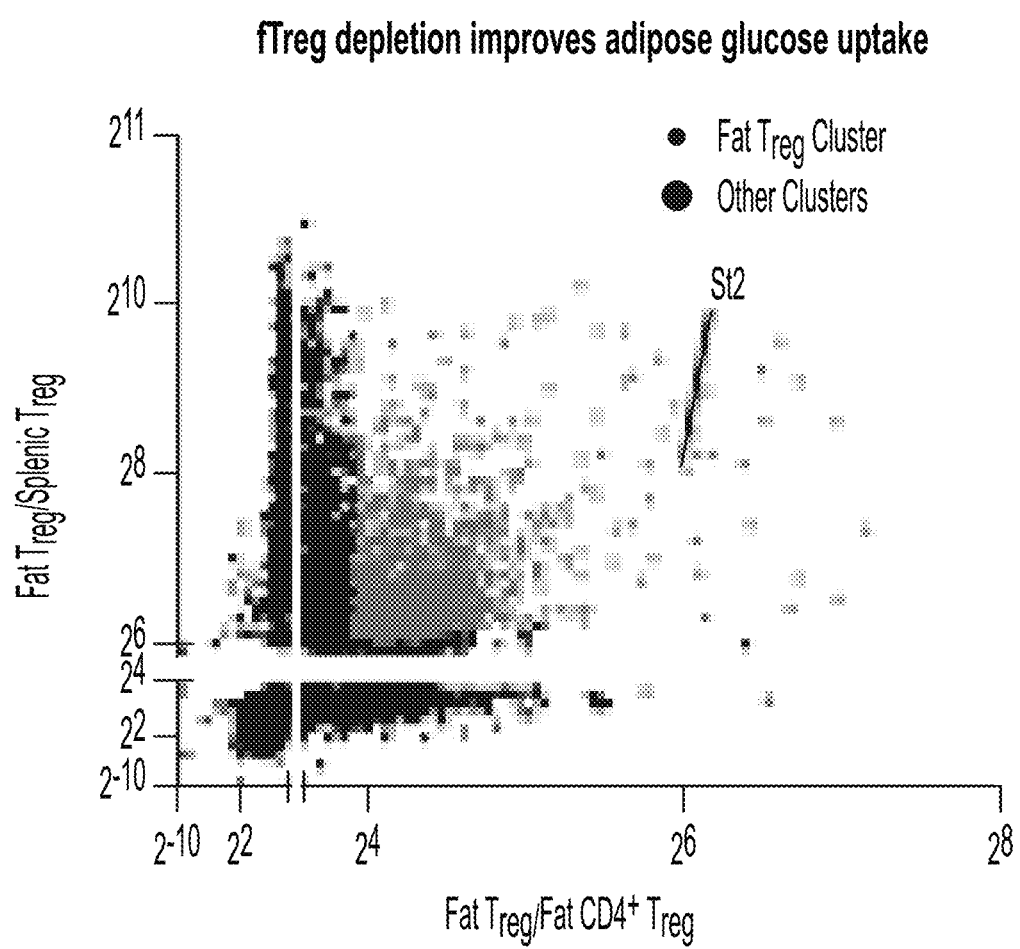
Figure 12C:
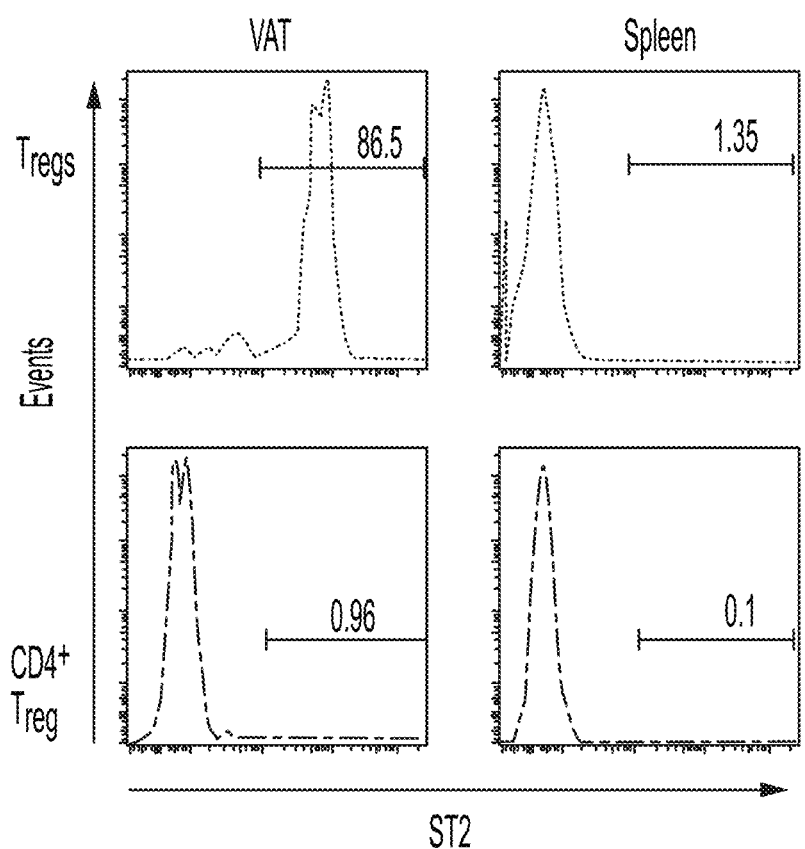
Figure 12D:
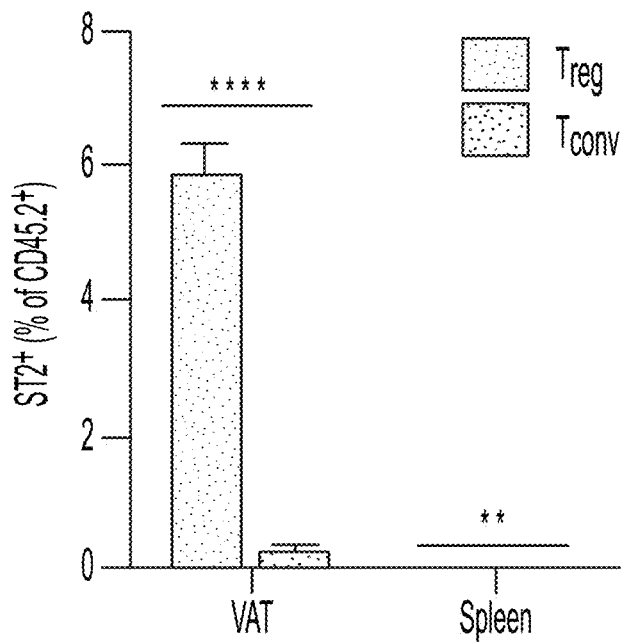
Figure 12E:
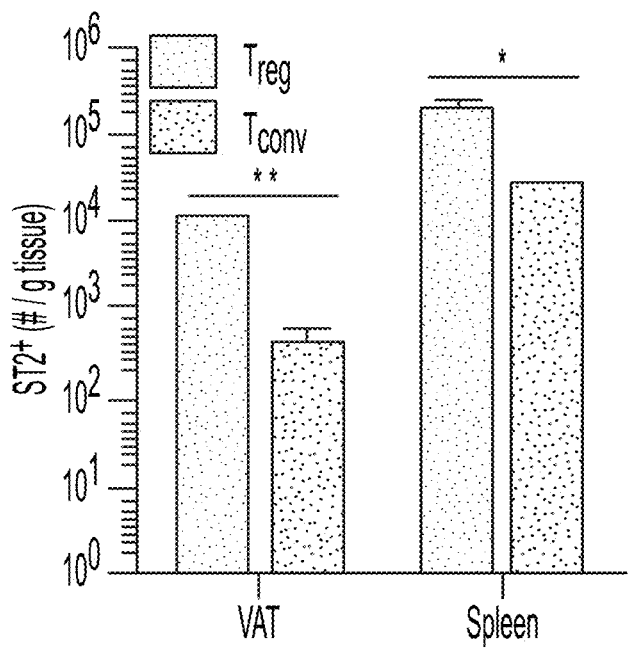

Example 5: fTregs are Functionally Distinct from Splenic Tregs and More Highly Express the IL-33 Receptor ST2 than Splenic Tregs or Conventional CD4+T (Tconv) Cells These findings of an association between fat-resident regulatory T cells (fTregs) and age-associated insulin resistance and metabolic aging indicated that these cells were functionally distinct from splenic Tregs. To investigate this notion, the transcriptomes of Tregs were compared, as well as conventional CD4+ T cells, isolated from visceral adipose tissue and spleen. Comparative analyses revealed that while certain canonical genes were similarly expressed (e.g. Foxp3, Ctla4, and Tigit), visceral adipose tissue and splenic Tregs had discrete expression signatures, consistent with the indicated functional distinction. In particular, Pparg, Gata3, and Irf4 were selectively enriched in visceral adipose tissue, but not splenic Tregs (FIG. 11A). Furthermore, unbiased comparative gene expression analyses combined with hierarchical clustering defined extensive fat- and splenic-residence clusters (1142 genes and 1431 genes, respectively) relative to much smaller Pan-Treg Clusters 1 and 2 (56 and 162 genes, respectively). Transcriptionally, fTregs clustered more closely with fat conventional CD4+ T cells than splenic Tregs (FIG. 12A), indicating that the functional specification of fTregs was informed by their anatomical location within adipose tissue, as well as the expression of the Treg lineage-specifying transcription factor Foxp3. It was posited that the transcriptional differences between fTregs and splenic Tregs (found in the fTreg cluster of 1049 genes) might provide a therapeutic avenue to selectively manipulate fTreg populations. The IL-33 receptor ST2, which lies within the fTreg cluster, had been recently implicated in effector Treg and in particular fTreg development (Vasanthakumar et al., *Nat Immunol* 1-12. doi:10.1038/ni.3085), 2015; Schiering, C. et al., *Nature* 513, 564-568, 2014). Indeed, ST2 was ~60 and ~30 times more highly expressed in fTregs compared to splenic Tregs and fat conventional CD4+ T cells, respectively, consistent with the ImmGen database (website of the Immunological Genome Project), (FIG. 12B and FIG. 11B). Flow cytometry confirmed that ST2 was expressed on the cell surface of the majority of fTregs, but on relatively few fat conventional CD4+ T cells, or splenic Tregs or conventional CD4+ T cells (FIG. 12C and FIG. 12D). Furthermore, visceral adipose tissue had ~10× more ST2+ fTregs than ST2+ fat conventional CD4+ T; a similar ratio was seen in the spleen (FIG. 12E).

Figure 12F:
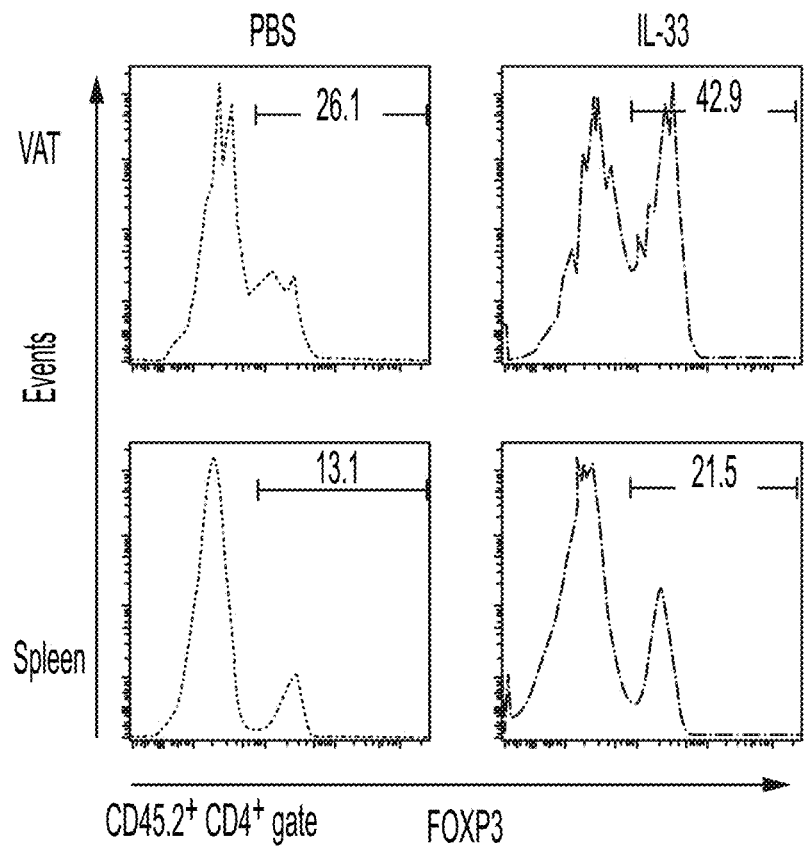
Figure 12G:
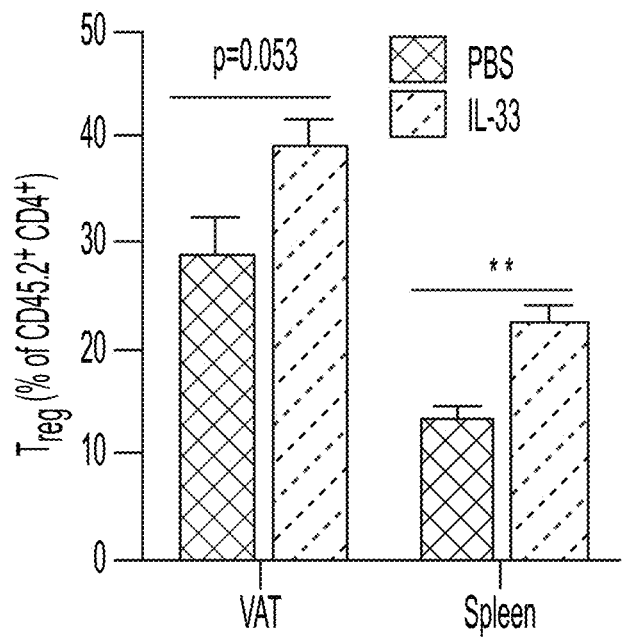
Figure 12H:
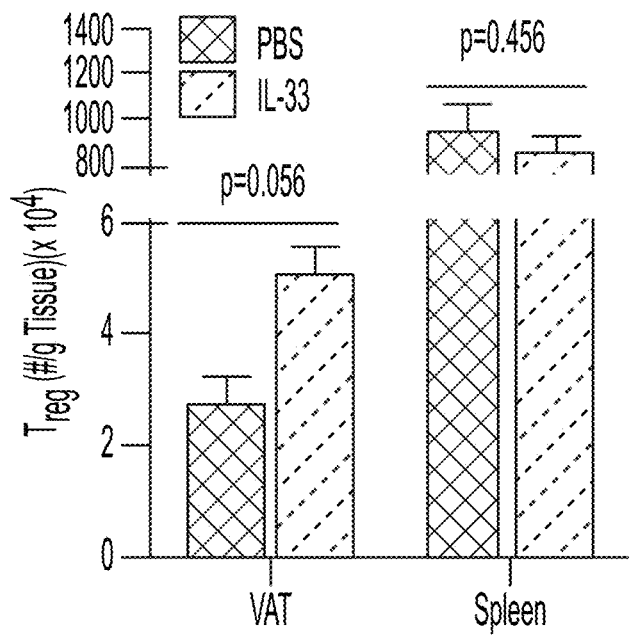
Figure 12I:
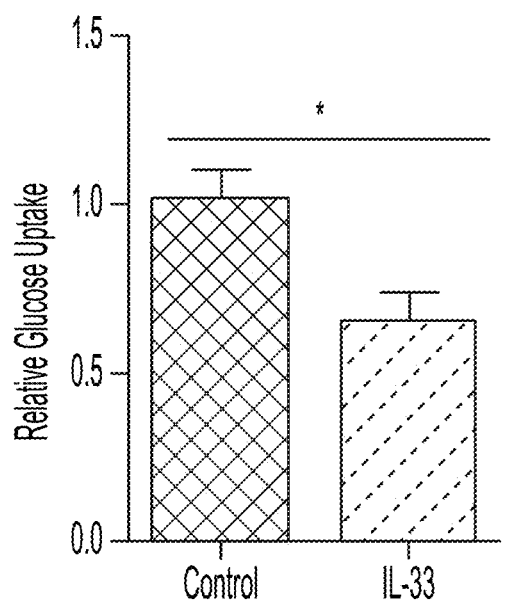
Figure 12J:
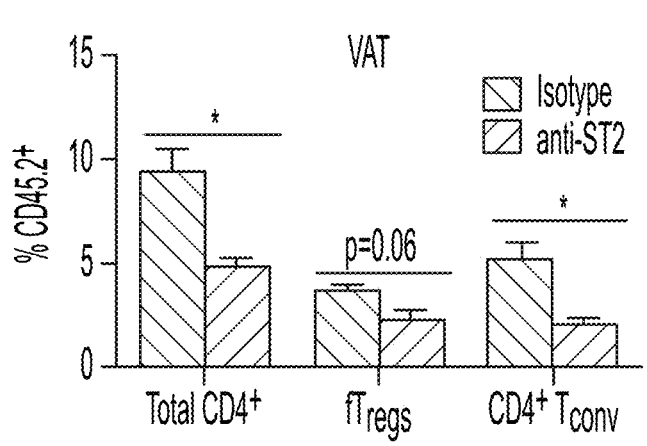
Figure 12K:
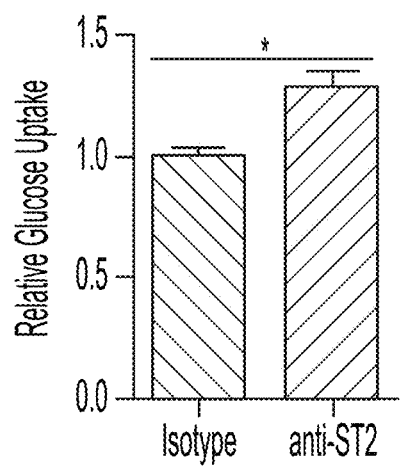
Figure 13A:
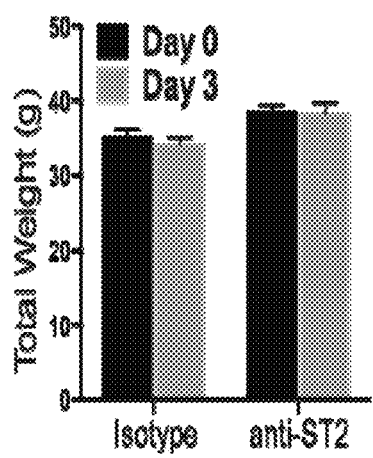
FIGS. 13A-13C are three bar graphs showing that depleting anti-ST2 antibody treatment does not promote T cell activation associated with systemic Treg-dysfunction.
Figure 13B:
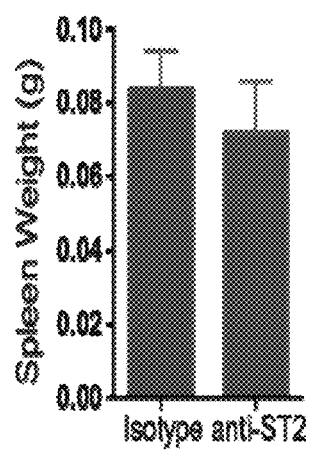
Figure 13C:
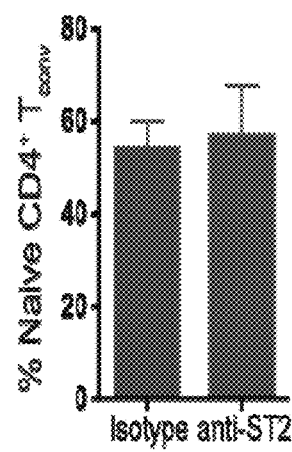

Example 6: Acute Treatment with an Anti-ST2 Antibody LED to Partial Depletion of fTregs Concomitantly with a Reduction in Fat CD4+T (Tconv) Cells and an Increase in Insulin Sensitivity To explore the therapeutic potential of the IL-33/ST2 signaling pathway, aged mice were initially injected with IL-33 (0.5 mg intraperitoneally (i.p.) on days 0, 2, 4) to expand the fat-resident regulatory T cell (fTreg) population (FIGS. 12F-12H). In agreement with fTreg expansion driven by IL2/anti-IL2 treatment, mice injected with IL-33 displayed signs of insulin resistance (basal glucose uptake in visceral adipose tissue reduced to ~60% of control mice, FIG. 12I). In the converse approach, acute treatment with an anti-ST2 antibody (200 mg/mouse i.p. on days 0 and 2) was able to partially deplete fTregs (FIG. 12J). This depletion occurred concomitantly with a reduction in fat CD4+ T (Tconv) cells, indicating a possible role for ST2 and/or fTregs in maintaining this population. Importantly, partial depletion of fTregs achieved with acute anti-ST2 treatment was sufficient to increase insulin-stimulated glucose uptake in visceral adipose tissue (~25% increase in glucose uptake compared to control treated mice, FIG. 12K). Furthermore, this increase in insulin sensitivity was achieved without any signs of conventional CD4+ T cell activation associated with systemic Treg dysfunction (FIGS. 13A-13C).

Figure 12L:
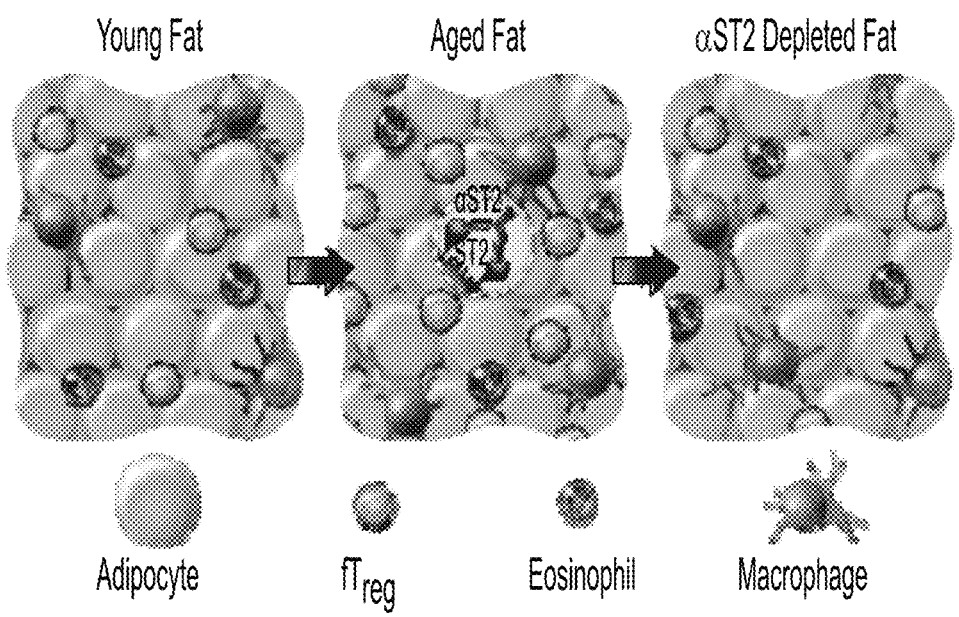

Taken together, these data provide evidence that distinct adipo-immune populations drive age- and obesity-associated insulin resistance. The findings that fTregs accumulated in mouse adipose tissue as a function of age and exacerbated the decline of adipose metabolic function associated with aging (FIG. 12L), complements the established role of M1 ATMs in the decline of adipose metabolic function in the setting of obesity. Thus, these studies showcased the ability of the immune compartment within adipose to drive key aspects of metabolic aging, in particular insulin resistance. Given the classical immune suppressive and anti-inflammatory nature of Tregs, it was speculated that the chronic inflammatory processes that drove obesity-associated insulin resistance were likely not driving age-associated insulin resistance. Indeed, it was possible that maintaining a certain degree of inflammation was beneficial for adipose tissue remodeling and its metabolic function, and the increased abundance of fTregs in the aged state might prevent beneficial inflammatory processes like adipose remodeling necessary for maintenance of adipose insulin sensitivity. Finally, this study indicated that selective targeting of fTregs might represent a new therapeutic avenue in the treatment of age-related diabetes, and more generally provided a proof-of-principle that different subtypes of Tregs could be targeted in a clinically achievable manner bringing researchers closer to the promise that the identification of Tregs heralded many years ago.

The experiments above were performed with the following methods and materials.

Methods and Materials

Mice

All mice were bred or housed in specific pathogen-free facilities at The Salk Institute for Biological Studies or purchased from Taconic Biosciences. C57BL/6NTac and 129S6/SvEvTac mice were purchased from Taconic Biosciences for comparative adipo-immune profiling (AIP). Age-matched retired breeders were purchased for AIP of aged adipose, and DIO C57BL/6NTac mice were purchased for profiling of obese adipose. fTreg KO mice were generated by crossing B6.129(Cg)-Foxp3$^{tm4(YFP/cre)Ayr}$/J (Rubtsov, Y. P. et al., *Immunity* 28, 546-558, 2008) and B6.129-Pparg$^{tm2Rev}$/J (He et al., PNAS 100, 15712-15717, 2003) mice. The Foxp3$^{Thy1.1}$ reporter mice were utilized when isolating Tregs and conventional CD4+ T cells from spleen and fat for subsequent RNA-Seq analysis. Mice within The Salk Institute for Biological Studies received autoclaved normal chow (MI laboratory rodent diet 5001, Harlan Teklad) or autoclaved HFD (60 kcal % fat, Research Diets). All mice used for studies were male.

Adipo-Immune Profiling (AIP)

Visceral (epididymal) and subcutaneous (inguinal) adipose depots were dissected from mice after 10 mL PBS perfusion through left ventricle. Inguinal lymph nodes resident in inguinal adipose were removed. Adipose was minced into fine pieces (2-5 mm$^3$) and digested in adipocyte isolation buffer (100 mM HEPES pH7.4, 120 mM NaCl, 50 mM KCl, 5 mM glucose, 1 mM CaCl2, 1.5% BSA) containing 1 mg/ml collagenase at 37° C. with intermittent shaking for 1.5 hours. The suspension was then passed through a 100 µm mesh to remove undigested clumps and debri. The flow-through was allowed to stand for 10 minutes to separate the floating adipocyte fraction and infranatant containing the stromal vascular fraction. The infranatant was removed while minimally disturbing the floating adipocyte fraction and centrifuged at 400 g for 10 minutes. The pellet containing the stromal vascular fraction was washed once in 10 mL RPMI. The resultant isolated cells were subjected to Fluorescence Activated Cell Sorting (FACS) analysis. The following antibodies were used to assemble the Adipo-immune Profile with the manufacturer preceding and clone number within parantheses: BioLegend—CD45.2 (104), CD44 (IM7), CD62L (MEL-14), TCRg/d (GL3), CD19 (6D5), CD25 (PC61), CD206 (C068C2), CD301 (LOM-14); eBioscience—CD3 (145-2C11), CD25 (PC61), CD4 (RM4-5), TCRb (H57-597), B220 (RA3-6B2), NK1.1 (PK136), CD49b (DX5), Foxp3 (FJK-16s), F4/80 (BM8), CD11c (N418), CD11b (M1/70); Tonbo biosciences—F4/80 (BM8.1), CD4 (RM4-5), CD44 (IM7), CD62L (MEL-14), Ly6G (RB6-8C5); BD Pharmingen—Siglec-F (E50-2440); BD Biosciences—CD8a (53-6.7). When analyzing myeloid cell populations, Fc blocking antibody (CD16/CD32, Tonbo biosciences, 2.4G2) was utilized. Cells were analyzed using the BD® FACS Aria instrument and FlowJo software.

Body Composition and Adipocyte Size Analyses

Body composition was measured with an ECHO® MRI-100 body composition analyzer (ECHO MEDICAL SYSTEMS®). Visceral adipose tissue (VAT) (epididymal adipose) was dissected, and the wet weight was determined. Adipose tissues were fixed in 10% formalin, sectioned, and stained in hematoxylin and eosin. An adipocyte cross-sectional area was determined from photomicrographs of VAT using ImageJ.

In Vivo Metabolic Phenotype Analysis

Real-time metabolic analyses were conducted in a Comprehensive Lab Animal Monitoring System (COLUMBUS INSTRUMENTS®). $CO_2$ production, $O_2$ consumption, and ambulatory counts were determined for at least three consecutive days and nights after at least 24 hours for adaptation before data recording.

Principal Component Analysis (PCA) of Adipo-Immune Profiling (AIP)

Non-macrophage immune cell populations, described as percent of the total CD45.2$^+$ immune compartment, were inputted into MetaboAnalyst 3.0 (a comprehensive tool suite for metabolomic data analysis) for principal component analysis (PCA). No normalizations, transformations, or scalings were implemented.

Glucose Homeostasis Studies

Fasting was induced for 6 hours, except for glucose tolerance tests (GTTs), which were conducted after overnight fasting. Glucose (1-2 g/kg, intraperitoneally (i.p.)) and insulin (0.5-1.0 U/kg, i.p.) was injected for GTTs and insulin tolerance tests (ITTs), respectively. Blood glucose was monitored using a Nova Max Plus glucometer.

Histological Analyses

Sections (4 mm) of fixed tissues were stained with haematoxylin and eosin according to standard procedures. Histopathological scores were graded on blinded samples for severity and extent of inflammation and morphological changes by a pathologist.

Serum Analyses

Blood was collected by tail bleeding or right atrial puncture. Non-esterified fatty acids (Wako) and triglycerides (Thermo) were measured using colorimetric methods. Serum insulin levels (ULTRA SENSITIVE INSULIN™, CRYSTAL CHEM®) were measured by ELISAs. Serum cytokine and metabolic hormone levels were analyzed by the LUMINEX™ BIO-PLEX® system using the Mouse Cytokine 23-Plex Panel and Diabetes Panel, respectively, as according to the manufacturer's instructions (BIO-RAD®).

Core Body Temperature

Mice were single housed, and core body temperature was measured with a clinical rectal thermometer (THERMALERT™ model TH-5; PHYSITEMP®) at 1:30 PM. The probe was dipped in a room temperature lubricating glycerol before insertion.

Ex Vivo 2-DG Uptake Assay

Adipose was dissected from mouse, cut into small pieces with scissors, washed and incubated for 30 minutes with Krebs-Ringer Bicarbonate HEPES buffer (KRBH, 120 mM NaCl, 4 mM $KH_2PO_4$, 1 mM $MgSO_4$, 0.75 mM $CaCl_2$, 30 mM Hepes, 10 mM $NaHCO_3$, pH 7.4, supplemented with 1% fatty-acid free BSA). For determination of exogenous insulin-stimulated 2-deoxy-D-glucose (2-DG) uptake, adipose was incubated in KRBH with 100-200 nM insulin for 20 minutes in 37° C. Cold 2-DG and hot 2-DG-1,2-$^3$H(N) was added to incubated adipose such that the final concentration of cold 2-DG was 0.1 mM and final quantity of hot 2-DG-1,2-$^3$H(N) was 0.1 µCi (assuming total reaction volume ~400 uL). Adipose was further incubated 20 minutes in 37° C., then washed three times with PBS before being lysed by scintillation fluid. 2-DG uptake was determined by measuring scintillation counts normalized to adipose mass utilized for assay. Non-specific 2-DG uptake levels were determined by treating adipose with cytochalasin B (0.1 µM final concentration) before addition of cold and hot 2-DG.

IL-2-Anti-IL-2 Complex and IL-33 Injections

IL-2-anti-IL-2 complexes were prepared by incubating 2 µg of murine IL-2 (Biolegend) with 10 µg of anti-IL-2 antibody (JES6.1, BIOXCELL®) in a total volume of 200 µL of PBS for 30 minutes at 37° C. (amounts given per injection). Mice were injected intraperitoneally (i.p.) three times (days 0, 1, 2) and analyzed on day 8. For IL-33 expansion assays, mice were injected i.p. with 0.5 µg of recombinant murine IL-33 in PBS (R&D SYSTEMS®) three times (days 0, 2, 4) and analyzed on day 6. PBS was used for control injections.

RNA-Seq Library Generation

Total RNA was isolated from sorted cells using TRIZOL® reagent (IINVITROGEN®) as per the manufacturer's instructions and treated with DNASEI® (QIAGEN®) for 30 minutes at 22° C. Sequencing libraries were prepared from 10-100 ng of total RNA using the TRUSEQ® RNA sample preparation kit v2 (ILLUMINA®) according to the manufacturer's protocol. Briefly, mRNA was purified, fragmented and used for first- and second-strand cDNA synthesis followed by adenylation of 3' ends. Samples were ligated to unique adaptors and subjected to PCR amplification. Libraries were then validated using the 2100 BIOANALYZER® (AGILENT®), normalized and pooled for sequencing. RNA-Seq libraries prepared from two biological replicates for each experimental condition were sequenced on the ILLUMINA® HISEQ® 2500 using barcoded multiplexing and a 100-bp read length.

High-Throughput Sequencing and Analysis

Image analysis and base calling were done with ILLUMINA® CASAVA®-1.8.2. This yielded a median of 29.9M usable reads per sample. Short read sequences were mapped to a UCSC mm9 reference sequence using the RNA-Seq aligner STAR® (Dobin, A. et al., *Bioinformatics* 29, 15-21, 2012). Known splice junctions from mm9 were supplied to the aligner and de novo junction discovery was also permitted. Differential gene expression analysis, statistical testing and annotation were performed using CUFFDIFF® 2 (Trapnell et al., Nat Biotechnol 31, 46-53, 2012). Transcript expression was calculated as gene-level relative abundance in fragments per kilobase of exon model per million mapped fragments and employed correction for transcript abundance bias (Roberts et al., Bioinformatics 27, 2325-2329, 2011). RNA-Seq results for genes of interest were also explored visually using the UCSC Genome Browser.

Hierarchical Clustering

Differentially expressed gene names and corresponding fragments per kilobase of exon per million fragments mapped (FPKM) values across samples were inputted into GENE-E (Broad Institute) for hierarchical clustering analysis (implemented one minus pearson correlation for sample and gene distance metrics and the average linkage method) and visualization. Gene cluster names were created to describe the gene expression characteristics within each cluster (i.e. Fat-Residence Cluster refers to the gene cluster whose genes were expressed at greater levels in T cells residing in fat. Fat-Treg Cluster refers to the gene cluster whose genes were expressed highest in only the fTregs).

ST2 Studies and Anti-ST2 Depleting Antibody Treatment

Fluorescence Activated Cell Sorting (FACS) antibody for ST2 was purchased from MD BIOPRODUCTS®, clone DJ8. Mice were injected intraperitoneally (i.p.) with 200 µg depleting anti-ST2 antibodies (Monticelli et al., Nat Immunol 12, 1045-1054, 2011; R&D® systems, clone 245707) or isotype control (BIOXCELL®) twice (days 0, 2) and sacrificed for analysis on day 3.

Statistical Analyses

Statistical analyses were performed with Prism 6.0 (GraphPad). p values were calculated using two-tailed unpaired Student's t test. When analyzing adipo-immune profiles, a false discovery rate approach was utilized to avoid the problem of an inflated false-positive rate due to the substantial number of hypothesis tests.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of reducing insulin resistance in a subject who has insulin resistance or who is identified as being at risk of developing insulin resistance, the method comprising administering to a subject in need thereof an anti-ST2 antibody or an antigen binding fragment thereof, wherein prior to said anti-ST2 antibody administration, the subject is identified as having insulin resistance or as being at risk of developing insulin resistance by measuring in a sample obtained from the subject an increase in an ST2 polypeptide or polynucleotide expression in a fat-resident regulatory T (fTreg) cell or an increase in the number of fTreg cells compared with a normal control.

2. The method of claim 1, wherein the subject has age-related insulin resistance.

3. The method of claim 1, wherein the subject is at risk of developing age-related insulin resistance.

4. The method of claim 1, wherein the subject is at least 50 years old.

5. The method of claim 1, wherein the subject is at least 60 years old.

6. The method of claim 1, wherein the fTreg cell is an adipocyte.

7. The method of claim 1, wherein the fTreg cell is present in a tissue biopsy.

8. The method of claim 7, wherein the tissue biopsy is obtained from visceral adipose tissue.

9. The method of claim 1, wherein the increase in the ST2 polypeptide is measured in an immunoassay.

10. The method of claim 1, wherein the anti-ST2 antibody or an antigen binding fragment thereof is administered to the subject parenterally.

11. The method of claim 1, wherein administering the anti-ST2 antibody or an antigen binding fragment thereof to the subject reduces body weight relative to a reference.

12. The method of claim 1, wherein administering the anti-ST2 antibody or an antigen binding fragment thereof to the subject reduces fasting serum glucose and insulin levels relative to a reference.

13. The method of claim 1, wherein administering the anti-ST2 antibody or an antigen binding fragment thereof to the subject increases respiratory exchange ratio, oxygen consumption, and/or core body temperature relative to a reference.

14. The method of claim 1, wherein administering the anti-ST2 antibody or an antigen binding fragment thereof to the subject increases the glucose uptake capacity of visceral adipose tissue relative to a reference.

15. The method of claim 1, wherein administering the anti-ST2 antibody or an antigen binding fragment thereof to the subject reduces serum non-esterified free fatty acid (NEFA) levels relative to a reference.

16. The method of claim 1, wherein administering the anti-ST2 antibody or an antigen binding fragment thereof to the subject specifically decreases fTreg numbers while preserving splenic Treg numbers in the subject.

\* \* \* \* \*